United States Patent
Sinclair et al.

(10) Patent No.: US 11,298,070 B2
(45) Date of Patent: Apr. 12, 2022

(54) SYSTEMS AND METHODS FOR MONITORING NEURAL ACTIVITY

(71) Applicant: DEEP BRAIN STIMULTATION TECHNOLOGIES PTY. LTD., East Melbourne (AU)

(72) Inventors: Nicholas Sinclair, East Melbourne (AU); Hugh McDermott, East Melbourne (AU); James Fallon, East Melbourne (AU); Thushara Perera, East Melbourne (AU); Arthur Wesley Thevathasan, East Melbourne (AU); Kristian Bulluss, East Melbourne (AU)

(73) Assignee: DEEP BRAIN STIMULATION TECHNOLOGIES PTY LTD, East Melbourne (AU)

( * ) Notice: Subject to any disclaimer, the term of this patent is extended or adjusted under 35 U.S.C. 154(b) by 67 days.

(21) Appl. No.: 16/616,017

(22) PCT Filed: May 21, 2018

(86) PCT No.: PCT/AU2018/050486
§ 371 (c)(1),
(2) Date: Nov. 22, 2019

(87) PCT Pub. No.: WO2018/213872
PCT Pub. Date: Nov. 29, 2018

(65) Prior Publication Data
US 2020/0138324 A1    May 7, 2020

(30) Foreign Application Priority Data

May 22, 2017 (AU) .............................. 2017901934
Aug. 2, 2017 (WO) ............... PCT/AU2017/050809

(51) Int. Cl.
*A61N 1/36* (2006.01)
*A61B 5/377* (2021.01)
(Continued)

(52) U.S. Cl.
CPC ............ *A61B 5/377* (2021.01); *A61B 5/4836* (2013.01); *A61N 1/0534* (2013.01);
(Continued)

(58) Field of Classification Search
CPC ......... A61B 5/316; A61B 5/4094; A61B 5/24; A61B 5/726; A61N 1/0529; A61N 1/36082; A61N 1/36171; A61N 1/3606
See application file for complete search history.

(56) References Cited

U.S. PATENT DOCUMENTS

| 5,561,526 A | 10/1996 | Huber et al. |
| 5,966,473 A | 10/1999 | Takahashi et al. |
(Continued)

FOREIGN PATENT DOCUMENTS

| AU | 2007281311 A1 | 2/2008 |
| AU | 2002340189 B2 | 8/2008 |
(Continued)

OTHER PUBLICATIONS

Written Opinion issued in PCT Patent Application No. PCT/AU2018/050486 dated Sep. 18, 2018.
(Continued)

*Primary Examiner* — Jon Eric C Morales
(74) *Attorney, Agent, or Firm* — Marshall, Gerstein & Borun LLP

(57) ABSTRACT

A method for monitoring neural activity responsive to a stimulus in a brain, the method comprising: a. applying a first stimulus to one or more of at least one electrode implanted in the brain, the first stimulus comprising a first plurality of bursts of stimulation, b. detecting high frequency
(Continued)

oscillations (HFOs) between about 200 Hz and about 500 Hz due to neuronal activity at one or more of the at least one electrode implanted in the brain at least partially during application of the first stimulus; c. determining one or more waveform characteristics of the HFOs; and d. generating a second stimulus comprising a second plurality of bursts of stimulation, wherein one or more waveform characteristics of the second stimulus is dependent on the one of more waveform characteristics of the HFOs; and e. applying the second stimulus to one or more of the at least one electrode implanted in the brain.

20 Claims, 24 Drawing Sheets

(51) Int. Cl.
    *A61B 5/00*         (2006.01)
    *A61N 1/05*         (2006.01)

(52) U.S. Cl.
    CPC ..... *A61N 1/36067* (2013.01); *A61N 1/36082* (2013.01); *A61N 1/36139* (2013.01); *A61N 1/36146* (2013.01)

(56) References Cited

U.S. PATENT DOCUMENTS

| | | | |
|---|---|---|---|
| 6,066,163 A | 5/2000 | John | |
| 6,137,491 A | 10/2000 | Szeliski | |
| 6,463,328 B1 | 10/2002 | John | |
| 6,480,743 B1 | 11/2002 | Kirkpatrick et al. | |
| 6,922,632 B2 | 7/2005 | Foxlin | |
| 6,985,238 B2 | 1/2006 | Isaacs et al. | |
| 7,639,741 B1 | 12/2009 | Holt et al. | |
| 7,768,626 B2 | 8/2010 | Lapa et al. | |
| 7,912,673 B2 | 3/2011 | Hebert et al. | |
| 7,983,757 B2 | 7/2011 | Miyazawa et al. | |
| 8,032,327 B2 | 10/2011 | Hebert et al. | |
| 8,082,120 B2 | 12/2011 | St-Pierre et al. | |
| 8,121,399 B2 | 2/2012 | Hayashi et al. | |
| 8,190,251 B2 | 5/2012 | Molnar et al. | |
| 8,662,676 B1 | 3/2014 | Chang et al. | |
| 8,791,997 B2 | 7/2014 | Munkelt et al. | |
| 8,798,764 B2 | 8/2014 | Molnar et al. | |
| 8,892,208 B2 | 11/2014 | Flynn et al. | |
| 8,914,119 B2 | 12/2014 | Wu et al. | |
| 9,325,973 B1 | 4/2016 | Hazeghi et al. | |
| 9,338,447 B1 | 5/2016 | Crump et al. | |
| 10,463,860 B2 | 11/2019 | Sinclair et al. | |
| 10,463,862 B2 | 11/2019 | LeBaron et al. | |
| 2002/0097906 A1 | 7/2002 | Ishiyama | |
| 2002/0135165 A1 | 9/2002 | Zayan et al. | |
| 2003/0097159 A1 | 5/2003 | Schiff et al. | |
| 2003/0234941 A1 | 12/2003 | Mundy et al. | |
| 2004/0057057 A1 | 3/2004 | Isaacs et al. | |
| 2004/0153129 A1 | 8/2004 | Pless et al. | |
| 2004/0252230 A1 | 12/2004 | Winder | |
| 2005/0021104 A1 | 1/2005 | DiLorenzo | |
| 2006/0062449 A1 | 3/2006 | Pratt | |
| 2006/0104495 A1 | 5/2006 | Cathier et al. | |
| 2006/0276722 A1 | 12/2006 | Litvak et al. | |
| 2007/0103646 A1 | 5/2007 | Young | |
| 2007/0142874 A1 | 6/2007 | John | |
| 2007/0183666 A1 | 8/2007 | Ding | |
| 2008/0004537 A1 | 1/2008 | Uutela | |
| 2008/0075324 A1 | 3/2008 | Sato et al. | |
| 2008/0097658 A1 | 4/2008 | Shue et al. | |
| 2008/0201101 A1 | 8/2008 | Hebert et al. | |
| 2008/0285843 A1 | 11/2008 | Lim | |
| 2009/0097039 A1 | 4/2009 | Kawasaki et al. | |
| 2009/0205088 A1 | 8/2009 | Crampton et al. | |
| 2009/0238449 A1 | 9/2009 | Zhang et al. | |
| 2010/0125315 A1 | 5/2010 | Parramon et al. | |
| 2010/0142805 A1 | 6/2010 | Maxwell et al. | |
| 2010/0142818 A1 | 6/2010 | Stein et al. | |
| 2010/0142825 A1 | 6/2010 | Maxwell et al. | |
| 2010/0142846 A1 | 6/2010 | Tolliver et al. | |
| 2010/0204748 A1 | 8/2010 | Lozano et al. | |
| 2011/0028859 A1 | 2/2011 | Chian | |
| 2011/0134225 A1 | 6/2011 | Saint-Pierre et al. | |
| 2011/0137371 A1 | 6/2011 | Giftakis et al. | |
| 2012/0016435 A1 | 1/2012 | Rom | |
| 2012/0065699 A1 | 3/2012 | Bedenbaugh | |
| 2012/0099798 A1 | 4/2012 | Saruta et al. | |
| 2012/0150257 A1* | 6/2012 | Aur ................ A61N 1/36171 607/45 |
| 2012/0271375 A1 | 10/2012 | Wu et al. | |
| 2013/0053722 A1 | 2/2013 | Carlson et al. | |
| 2013/0150918 A1 | 6/2013 | Peterson et al. | |
| 2014/0163627 A1 | 6/2014 | Starr et al. | |
| 2014/0276195 A1 | 9/2014 | Papay et al. | |
| 2015/0238765 A1 | 8/2015 | Zhu | |
| 2016/0074663 A1 | 3/2016 | De Ridder | |

FOREIGN PATENT DOCUMENTS

| | | |
|---|---|---|
| AU | 2014351064 B2 | 7/2019 |
| CA | 2656163 C | 7/2011 |
| CN | 101026776 A | 8/2007 |
| CN | 101292131 B | 7/2011 |
| CN | 102338616 A | 2/2012 |
| CN | 101611291 B | 4/2012 |
| CN | 101620676 B | 5/2012 |
| CN | 102263920 B | 5/2014 |
| EP | 1385426 B1 | 6/2005 |
| EP | 1335668 B1 | 7/2006 |
| EP | 1575664 B1 | 2/2010 |
| JP | H08136220 A | 5/1996 |
| JP | H1021401 A | 1/1998 |
| JP | 2000175176 A | 6/2000 |
| JP | 2002521683 A | 7/2002 |
| JP | 2009283917 A | 12/2009 |
| JP | 2012026974 A | 2/2012 |
| WO | WO-99/60525 A1 | 11/1999 |
| WO | WO-02/30510 A1 | 4/2002 |
| WO | WO-2004/043536 A1 | 5/2004 |
| WO | WO-2009/009724 A1 | 1/2009 |
| WO | WO-2011/119251 A2 | 9/2011 |
| WO | WO-2012168904 A3 | 2/2013 |
| WO | WO-2013/123112 A1 | 8/2013 |
| WO | WO-2015/069632 A1 | 5/2015 |
| WO | WO-2015/070281 A1 | 5/2015 |
| WO | WO-2015/079324 A2 | 6/2015 |
| WO | WO-2016/205231 A1 | 12/2016 |
| WO | WO-2018/005981 A1 | 1/2018 |
| WO | WO-2018/027259 A1 | 2/2018 |

OTHER PUBLICATIONS

International Search Report issued in PCT Patent Application No. PCT/AU2018/050486 dated Sep. 18, 2018.
Eusebio et al., Resonance in subthalamo-cortical circuits in Parkinson's disease, Brain, 132(Pt.8):2139-50 (Aug. 2009).
Westlye et al., Increased hippocampal default mode synchronization during rest in middle-aged and elderly APOE e4 carriers: relationships with memory performance, J. Neurosci., 31 (21):7775-83 (May 2011).
International Application No. PCT/AU2017/050809, International Search Report and Written Opinion, dated Nov. 29, 2017.
International Application No. PCT/AU2017/050809, Third Party Observation, submitted Dec. 6, 2018.
Kent et al., Recording evoked potentials during deep brain stimulation: development and validation of instrumentation to suppress the stimulus artefact, J. Neural Eng., 9(3):036004 (Jun. 2012).
Al-Ani et al., Automatic removal of high-amplitude stimulus artefact from neuronal signal recorded in the subthalamic nucleus, J. Neuroscience Methods, 198:135-46 (2011).
International Search Report issued in PCT Patent Application No. PCT/AU2019/050407 dated Jul. 11, 2019.

(56) References Cited

OTHER PUBLICATIONS

Zaehle et al., "Resonance phenomena in the human auditory cortex: individual resonance frequencies of the cerebral cortex determining electrophysiological responses," *Experimental Brain Research*, vol. 203, No. 3 (May 7, 2010).

Blais, F., "Review of 20 years of range sensor development," *Journal of Electronic Imaging*, vol. 13(1) (Jan. 2004).

Zhang, L. et al., "Rapid Shape Acquisition Using Color Structured Light and Multi-Pass Dynamic Programming," https://grail.cs.washington.edu/projects/moscan/paper.pdf.

Vuylsteke, P. et al., "Range Image Acquisition with a Single Binary-Encoded Light Pattern," *IEEE Transaction on Pattern Analysis and Machine Intelligence*, vol. 12, No. 2 (Feb. 1990).

Heikkila, J., "Geometric Camera Calibration Using Circular Control Points," *IEEE Transactions on Pattern Analysis and Machine Intelligence*, vol. 22, No. 10 (Oct. 2000).

Ouellet, J. et al., "Geometric Calibration of a Structured Light System Using Circular Control Points" *Proceedings of the Fourth 3D Data Processing Visualization and Transmission*, pp. 1-8 (Jun. 2008).

Salvi, J. et al., "Pattern Codification Strategies in Structured Light Systems," *Pattern Recognition*, vol. 37, pp. 827-849, (2004).

Trucco, E. et al., "Introductory Techniques for 3-D Computer Vision," pp. 292-293, (1998).

Gelfand, N. et al., "Geometrically Stable Sampling for the ICP Algorithm," Fourth International Conference on 3d Digital Imaging and Modeling, 9 pages (Oct. 2003).

Gelfand, N. et al., "Shape Segmentation Using Local Slippage Analysis," *Eurographics Symposium on Geometry Processing* (2004).

Herbert, P., "A Self-Referenced Hand-Held Range Sensor," *IEEE, Third International Conference on 3 D Digital Imaging and Modeling*, pp. 5-12 (2001).

Guehring, J. "Reliable 3D Surface Acquisition, Registration and Validation Using Statistical Error Models," *IEEE, Third International Conference on 3 D Digital Imaging and Modeling*, pp. 224-231 (2001).

Newcombe, R. et al, "KinectFusion: Real-Time Dense Surface Mapping and Tracking," *IEEE International Symposium on Mixed and Augmented Reality* (*ISMAR*), pp. 127-136 (2011).

Choi, C. et al., "Voting-based Pose Estimation for Robotic Assembly Using a 3D Sensor," *IEEE International Conference on Robotics and Automation* (*ICRA*), pp. 1824-1831 (2012).

\* cited by examiner

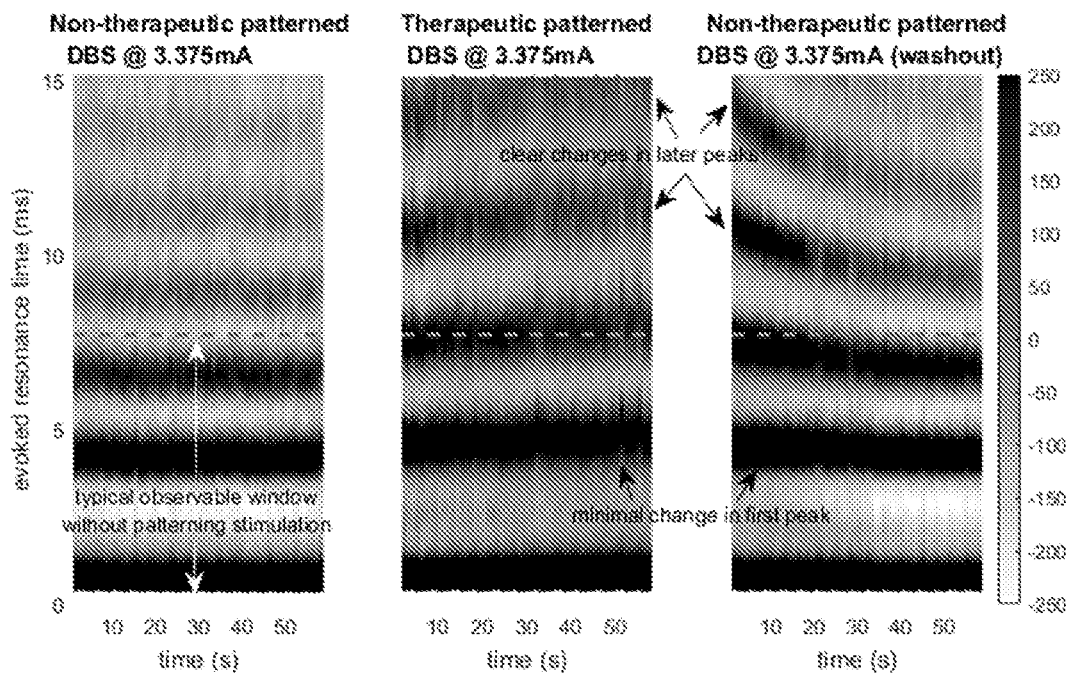
*Figure 5a*  *Figure 5b*  *Figure 5c*
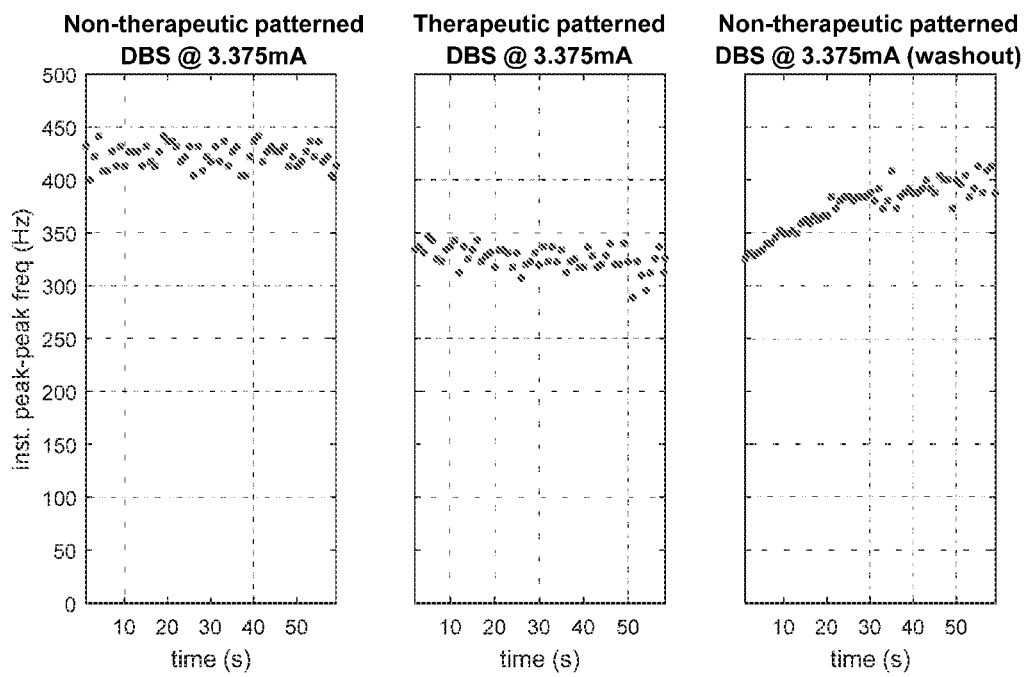
*Figure 5d*  *Figure 5e*  *Figure 5f*

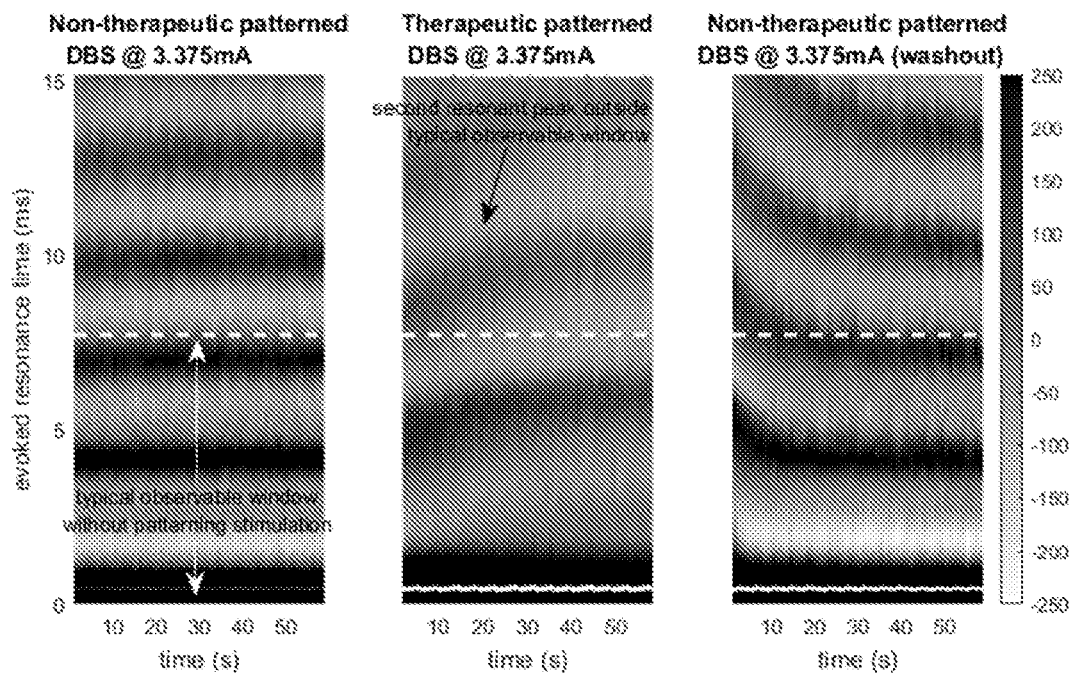
*Figure 6a*   *Figure 6b*   *Figure 6c*
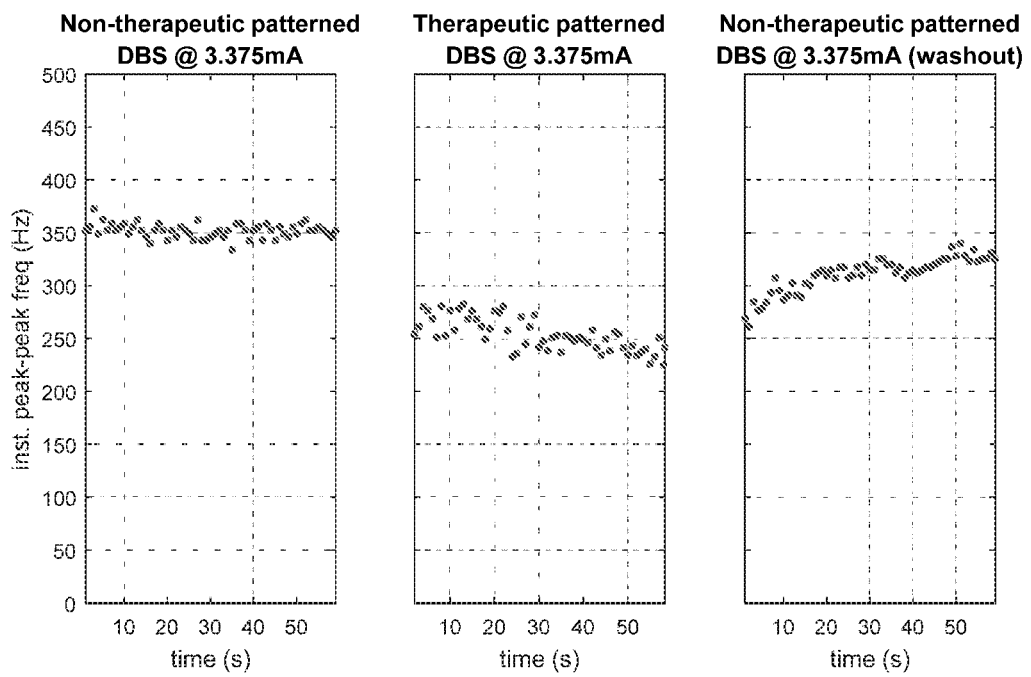
*Figure 6d*   *Figure 6e*   *Figure 6f*

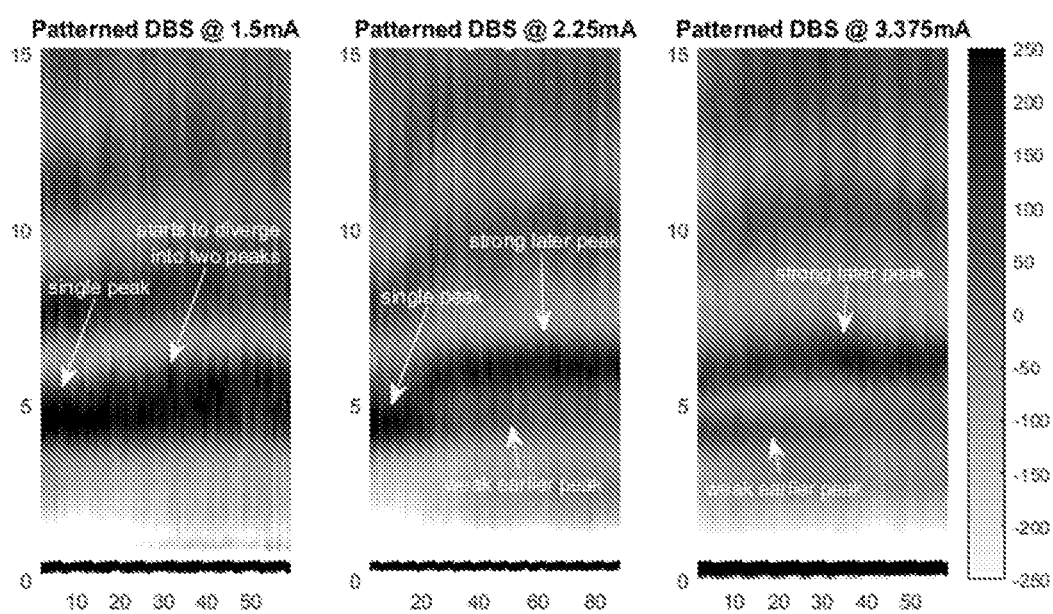
*Figure 7a*  *Figure 7b*  *Figure 7c*

SYSTEMS AND METHODS FOR MONITORING NEURAL ACTIVITY

RELATED APPLICATIONS

The present application claims priority from Australian provisional patent application number 2017901934 filed 22 May 2017, and International patent application number PCT/AU2017/050809, filed 2 Aug. 2017.

TECHNICAL FIELD

The present disclosure relates to deep brain stimulation (DBS) and, in particular, methods and systems of monitoring neural activity during DBS.

BACKGROUND

Deep brain stimulation (DBS) is an established therapy for movement disorders as well as other neurological disorders, including epilepsy, obsessive compulsive disorder, and depression. DBS is typically administered to patients whose symptoms cannot be adequately controlled by medication alone. DBS involves surgically implanting electrodes in or near to specific neural structures of the brain, typically in the subthalamic nucleus (STN), the globus pallidus interna (GPi), and/or the thalamus. Electrodes are connected to a neurostimulator usually implanted within the body and configured to deliver electrical pulses into target areas. It is believed that this electrical stimulation disrupts abnormal brain activity causally linked to a patient's symptoms. Stimulation parameters can be adjusted using a controller external to the body, remotely connected to the neurostimulator.

Whilst established DBS technology has proven to be effective in alleviating movement disorder symptoms, there are several limitations to state of the art devices. In particular, established techniques for intraoperative testing of DBS electrodes to ensure correct positioning in the brain, such as x-ray imaging, microelectrode recordings, and clinical assessment can be inaccurate. Consequently, electrodes are often implanted in suboptimal locations, resulting in diminished therapeutic outcomes and unwanted side-effects. After implantation, DBS devices require manual adjustment by a clinician. This typically involves the clinician adjusting parameters of the stimulus based on a largely subjective assessment of immediate or short-term improvement of the patient's symptoms. Since therapeutic effects can be slow to emerge and because the DBS parameter space is large, the task of finding a preferred set of parameters is time- and cost-inefficient, and can lead to suboptimal therapeutic outcomes. In addition, the constant, non-varying application of electrical stimulation using conventional DBS can also lead to suboptimal therapeutic outcomes, including unwanted side effects, as well as reduced battery life of DBS stimulators.

SUMMARY

According to a first aspect of the disclosure, there is provided a method for monitoring neural activity responsive to a stimulus in a brain, the method comprising:

a. applying a first stimulus to one or more of at least one electrode implanted in the brain, the first stimulus comprising a first plurality of bursts of stimulation, b. detecting high frequency oscillations (HFOs) due to neuronal activity at one or more of the at least one electrode implanted in the brain at least partially during application of the first stimulus;

c. determining one or more waveform characteristics of the HFOs; and d. generating a second stimulus comprising a second plurality of bursts of stimulation, wherein one or more waveform characteristics of the second stimulus is dependent on the one of more waveform characteristics of the HFOs; and e. applying the second stimulus to one or more of the at least one electrode implanted in the brain.

The first plurality of bursts may comprise a first burst applied for a first time period and having a first waveform characteristic and at least a second burst applied for a second time period following the first time period and having a second waveform characteristic.

Detecting HFOs due to neuronal activity at one or more of the at least one electrode implanted in the brain may further comprise: detecting a first high frequency oscillation (HFO) during the first time period and at least a second HFO during the second time period at one or more of the at least one electrode implanted in the brain.

The one or more waveform characteristics of the HFOs may comprise one or more waveform characteristics of the first and at least second HFOs.

The one or more waveform characteristics of the HFOs may comprise one or more of the following:
a) a frequency;
b) an amplitude;
c) a rate of change of frequency;
d) a rate of change of amplitude; and
e) a bandwidth.

The first and second waveform characteristics may comprise one or more of the following:
a) a frequency;
b) an amplitude;
c) a pulse width;
d) an interphase gap.

One or more of the plurality of bursts may comprise one of: a) a symmetric waveform having a first phase and a second phase of opposite polarity to the first phase; and b) a biphasic waveform having a first phase at a first amplitude for a first duration and a second phase of opposite polarity to the first phase, the second phase having a second amplitude and a second duration, the product of the first amplitude and the first duration being substantially equal to the product of the second amplitude and the second duration.

The first stimulus and/or the second stimulus may be a therapeutic stimulus or a non-therapeutic stimulus.

The first plurality of bursts may be separated by a first pattern time period, each of the first plurality of bursts comprising a plurality of pulses separated by a second pattern time period. The first pattern time period may be greater than the second pattern time period.

Equally, the second plurality of bursts may be separated by a first pattern time period, each of the first plurality of bursts comprising a plurality of pulses separated by a second pattern time period. The first pattern time period may be greater than the second pattern time period.

Alternatively, the first pattern time period may equal to the second pattern time period.

Two or more of pulses within at least one of the first plurality of bursts may have different amplitudes.

Two or more of pulses within at least one of the second plurality of bursts may have different amplitudes.

The different amplitudes may be selected to produce a ramp in amplitude of sequential pulses in the at least one of the bursts of the first plurality of bursts or the second plurality of bursts.

The amplitude of a final pulse in each of the first plurality of bursts may be substantially identical. Equally, the amplitude of a final pulse in each of the second plurality of bursts may be substantially identical.

The one or more waveform characteristics of the second stimulus may comprise a frequency which is configured in dependence of a characteristic of the detected HFOs.

The frequency may be configured to be equal to the frequency of the HFO divided by 1, 2, 3 or 4.

The one or more waveform characteristics of the HFOs may comprise a rate of change of frequency.

The one or more characteristics of the second stimulus may be configured to maximise the rate of change of the frequency of the HFOs.

The frequency of the HFOs being detected is preferably between 200 Hz and 500 Hz.

The method may further comprise: determining a correlation between the detected HFOs and a HFO template; and generating the second stimulus based on the correlation.

The method may further comprise: determining a correlation between the one or more determined waveform characteristics of the HFOs with one or more predetermined threshold values; and generating the second stimulus based on the correlation.

The method may further comprise: estimating a patient state of a patient based on the determined one or more waveform characteristics of the HFOs.

The method may further comprise: diagnosing the patient based on the estimate of the patient's state.

The method may further comprise: generating one or more alerts associated with the estimated patient state; and outputting the one or more alerts.

The method may further comprise: whilst applying the second stimulus, simultaneously detecting high frequency oscillations (HFOs) due to neuronal activity at one or more of the at least one electrode implanted in the brain; and determining one or more second waveform characteristics of the detected second resonant response.

The method may further comprise: estimating a degree of progression of a disease associated with the patient based on the one or more first waveform characteristics of the HFOs and the one or more second waveform characteristics of the HFOs.

The method may further comprise: determining the effect of a therapy provided to the patient based on the one or more first waveform characteristics of the HFOs and the one or more second waveform characteristics of the HFOs.

The therapy may comprise one or more of medication and deep brain stimulation.

The at least one electrode may comprise two or more electrodes located within different neural structures in the brain.

The at least one electrode may comprise two or more electrodes located within different hemispheres of the brain.

The method may further comprise: whilst applying the second stimulus, simultaneously determining one or more second waveform characteristics of the HFOs.

The method may further comprise: comparing a common waveform characteristic between the one or more waveform characteristics and the one or more second waveform characteristics.

The method may further comprise: comparing a degree of change of a common waveform characteristic between the one or more waveform characteristics and the one or more second waveform characteristics.

The method may further comprise: comparing a rate of change of a common waveform characteristic between the one or more waveform characteristics and the one or more second waveform characteristics.

The steps of applying the second stimulus whilst simultaneously determining one or more second waveform characteristics of the HFOs may be repeated until it is determined that one or more of the at least one electrode is positioned in a target neural structure in the brain.

The method may further comprise: selecting one or more of the at least one electrode to use for therapeutic stimulation of a target neural structure in the brain based on the one or more waveform characteristics or the one or more second waveform characteristics; and applying a therapeutic stimulus to the target neural structure via the selected one or more of the at least one electrode.

The method may further comprise: inserting the at least one electrode into the brain along a predefined trajectory; wherein the steps of applying the second stimulus whilst simultaneously determining one or more second waveform characteristics of the HFOs are repeated while the at least one electrode is being inserted to generate a profile of HFO activity with respect to the predefined trajectory and a target neural structure in the brain The profile of HFO activity may be used to determine a position of the one or more electrodes relative to the target neural structure.

The at least one electrode may comprise a plurality of electrodes. In which case, the steps of applying the second stimulus whilst simultaneously determining one or more second waveform characteristics of the HFOs may be repeated using different combinations of the at least one electrode to generate a profile of HFO activity for the different combinations of the at least one electrode.

The method may further comprise: selecting one or more of the at least one electrode based on the profile of HFO activity; and applying a therapeutic stimulus to the selected one or more of the at least one electrode.

The selected one or more of the at least one electrode may comprises a plurality of electrodes.

The method may further comprise:

e. detecting a resonant response from the target neural structure evoked by the stimulus at one or more of the at least one electrode in or near a target neural structure of the brain; and f. determining one or more waveform characteristics of the detected resonant response.

According to a further aspect of the disclosure, there is provided, a neuromodulation system, comprising:

a lead having at least one electrode adapted for implantation in or near a target neural structure in the brain;

a signal generator selectively coupled to one or more of the at least one electrode and configured to:

generate and apply a first stimulus to one or more of the at least one electrode, the first stimulus comprising a first plurality of bursts of stimulation; and generate and apply a second stimulus to one or more of the at least one electrode, the second stimulus comprising a second plurality of bursts of stimulation;

a measurement device selectively coupled to one or more of the at least one electrode and configured to detect high frequency oscillations (HFOs) generated from neural activity at one or more of the at least one electrode when implanted in the brain at least partially during application of the first stimulus; and a processing unit coupled to the measurement device and configured to determine one or more waveform characteristics of the detected HFOs, wherein one or more waveform characteristics of the second stimulus is dependent on the one of more waveform characteristics of the HFOs.

The first plurality of bursts may comprise a first burst applied for a first time period and having a first waveform characteristic and at least a second burst applied for a second time period following the first time period and having a second waveform characteristic.

The measurement device may be configured to: detect a first high frequency oscillation (HFO) during the first time period and at least a second HFO during the second time period at one or more of the at least one electrode implanted in the brain.

The one or more waveform characteristics of the HFOs may comprise one or more waveform characteristics of the first and at least second HFOs.

The one or more waveform characteristics of the HFOs may comprise one or more of the following:
a) a frequency;
b) an amplitude;
c) a rate of change of frequency;
d) a rate of change of amplitude
e) a bandwidth.

The first and second waveform characteristics may comprise one or more of the following:
a) a frequency;
b) an amplitude;
c) a pulse width;
d) an interphase gap.

One or more of the plurality of bursts may comprise one of: a) a symmetric waveform having a first phase and a second phase of opposite polarity to the first phase; and b) a biphasic waveform having a first phase at a first amplitude for a first duration and a second phase of opposite polarity to the first phase, the second phase having a second amplitude and a second duration, the product of the first amplitude and the first duration being substantially equal to the product of the second amplitude and the second duration.

The first stimulus and/or the second stimulus may be a therapeutic stimulus or a non-therapeutic stimulus.

The first plurality of bursts may be separated by a first pattern time period, each burst comprising a plurality of pulses separated by a second pattern time period. Additionally or alternatively, the first plurality of bursts may be separated by a first pattern time period, each burst comprising a plurality of pulses separated by a second pattern time period.

In either case, the first pattern time period may greater than the second pattern time period. Alternatively, the first pattern time period may be greater than or equal to the second pattern time period.

Two or more pulses within at least one of the first plurality of bursts may have different amplitudes. Additionally or alternatively, two or more of pulses within at least one of the second plurality of bursts may have different amplitudes.

The different amplitudes may be selected to produce a ramp in amplitude of sequential pulses in the at least one of the bursts of the first plurality of bursts or the second plurality of bursts.

The amplitude of a final pulse in each of the first plurality of bursts may be substantially identical. Additionally or alternatively, the amplitude of a final pulse in each of the second plurality of bursts may be substantially identical.

The one or more waveform characteristics of the second stimulus may comprise a frequency which is configured in dependence of the frequency the detected HFOs.

The frequency may be configured to be equal to the frequency of the first and/or second HFO divided by 1, 2, 3 or 4.

The one or more waveform characteristics of the HFOs may comprise a rate of change of frequency. The one or more characteristics of the one or more waveform characteristics of the second stimulus may be configured to maximise the rate of change of the frequency of the HFOs.

The frequency of the HFOs being detected is preferably between 200 Hz and 500 Hz.

The system may further correlating the detected HFOs with an HFO template; and generating the second stimulus based on the correlation.

The processing unit may be further configured to: determine a correlation between the detected HFOs and an HFO template; and generating the second stimulus based on the correlation.

The processing unit may be further configured to: determine a correlation between the one or more determined waveform characteristics of the HFOs and one or more predetermined threshold values; and generate the second stimulus based on the correlation.

The processing unit may be further configured to: estimate a patient state of a patient based on the determined one or more waveform characteristics of the HFOs.

The processing unit may be further configured to: diagnose the patient based on the estimate of the patient's state.

The processing unit may be further configured to: generate one or more alerts associated with the estimated patient state; and outputting the one or more alerts.

The processing unit may be further configured to: whilst applying the second stimulus, simultaneously detect high frequency oscillations (HFOs) due to neuronal activity at one or more of the at least one electrode implanted in the brain; and determine one or more second waveform characteristics of the detected HFOs during application of the second stimulus.

The processing unit may be further configured to: estimate a degree of progression of a disease associated with the patient based on the one or more first waveform characteristics of the HFOs and the one or more second waveform characteristics of the HFOs.

The processing unit may be further configured to: determine the effect of a therapy provided to the patient based on the one or more first waveform characteristics of the HFOs and the one or more second waveform characteristics of the HFOs.

The therapy may be medication or deep brain stimulation.

The at least one electrode may comprise two or more electrodes located within different neural structures in the brain.

The at least one electrode may comprise two or more electrodes located within different hemispheres of the brain.

The processing unit may be further configured to: whilst applying the second stimulus, simultaneously determine one or more second waveform characteristics of the HFOs.

The processing unit may be further configured to: compare a common waveform characteristic between the one or more waveform characteristics and the one or more second waveform characteristics.

The processing unit may be further configured to: compare a degree of change of a common waveform characteristic between the one or more waveform characteristics and the one or more second waveform characteristics.

The processing unit may be further configured to: compare a rate of change of a common waveform characteristic between the one or more waveform characteristics and the one or more second waveform characteristics.

The steps of applying the second stimulus whilst simultaneously determining one or more second waveform characteristics of the HFOs may be repeated until it is determined that one or more of the at least one electrode is positioned in a target neural structure in the brain.

The processing unit may be further configured to: select one or more of the at least one electrode to use for therapeutic stimulation of a target neural structure in the brain based on the one or more waveform characteristics or the one or more second waveform characteristics; and apply a therapeutic stimulus to the target neural structure via the selected one or more of the at least one electrode.

The processing unit may be further configured to: insert the at least one electrode into the brain along a predefined trajectory; wherein the steps of applying the second stimulus whilst simultaneously determining one or more second waveform characteristics of the HFOs are repeated while the at least one electrode is being inserted to generate a profile of HFO activity with respect to the predefined trajectory and a target neural structure in the brain The profile of HFO activity may be used to determine a position of the one or more electrodes relative to the target neural structure.

The at least one electrode may comprise a plurality of electrodes. In which case, the steps of applying the second stimulus whilst simultaneously determining one or more second waveform characteristics of the HFOs may be repeated using different combinations of the at least one electrode to generate a profile of HFO activity for the different combinations of the at least one electrode.

The processing unit may be further configured to: select one or more of the at least one electrode based on the profile of HFO activity; and apply a therapeutic stimulus to the selected one or more of the at least one electrode.

The selected one or more of the at least one electrode may comprise a plurality of electrodes.

The processing unit may be further configured to:

e. detect a resonant response from the target neural structure evoked by the stimulus at one or more of the at least one electrode in or near a target neural structure of the brain; and f. determine one or more waveform characteristics of the detected resonant response.

According to a further aspect of the disclosure, there is provided a method for monitoring neural activity responsive to a stimulus in a brain, the method comprising:

a. applying a first stimulus to one or more of at least one electrode implanted in the brain, the first stimulus comprising a first plurality of bursts of stimulation, b. detecting high frequency oscillations (HFOs) due to neuronal activity at one or more of the at least one electrode implanted in the brain at least partially during application of the first stimulus;

c. determining one or more waveform characteristics of the HFOs; and d. generating a second stimulus comprising a second plurality of bursts of stimulation, wherein one or more waveform characteristics of the second stimulus is dependent on the one of more waveform characteristics of the HFOs; and e. applying the second stimulus to one or more of the at least one electrode implanted in the brain, wherein the first plurality of bursts and/or the second plurality of bursts are separated by a first pattern time period, each burst comprising a plurality of pulses separated by a second pattern time period, wherein the first pattern time period is greater than the second pattern time period.

In some embodiments, two or more of pulses within at least one of the first plurality of bursts have different amplitudes. Additionally or alternatively, two or more of pulses within at least one of the second plurality of bursts have different amplitudes.

The different amplitudes may be selected to produce a ramp in amplitude of sequential pulses in the at least one of the bursts of the first plurality of bursts or the second plurality of bursts.

The amplitude of a final pulse in each of the first plurality of bursts may be substantially identical. Additionally or alternatively, the amplitude of a final pulse in each of the second plurality of bursts may be substantially identical.

According to a further aspect of the disclosure, there is provided a neuromodulation system, comprising:

a lead having at least one electrode adapted for implantation in or near a target neural structure in the brain;

a signal generator selectively coupled to one or more of the at least one electrode and configured to:

generate and apply a first stimulus to one or more of the at least one electrode, the first stimulus comprising a first plurality of bursts of stimulation; and generate and apply a second stimulus to one or more of the at least one electrode, the second stimulus comprising a second plurality of bursts of stimulation;

a measurement device selectively coupled to one or more of the at least one electrode and configured to detect high frequency oscillations (HFOs) generated from neural activity at one or more of the at least one electrode when implanted in the brain at least partially during application of the first stimulus; and a processing unit coupled to the measurement device and configured to determine one or more waveform characteristics of the detected HFOs, wherein one or more waveform characteristics of the second stimulus is dependent on the one of more waveform characteristics of the HFOs, wherein the first plurality of bursts and/or the second plurality of bursts are separated by a first pattern time period, each burst comprising a plurality of pulses separated by a second pattern time period, wherein the first pattern time period is greater than the second pattern time period.

In some embodiments, two or more pulses within at least one of the first plurality of bursts have different amplitudes. Additionally or alternatively, two or more of pulses within at least one of the second plurality of bursts may have different amplitudes.

The different amplitudes may be selected to produce a ramp in amplitude of sequential pulses in the at least one of the bursts of the first plurality of bursts or the second plurality of bursts.

The amplitude of a final pulse in each of the first plurality of bursts may be substantially identical. The amplitude of a final pulse in each of the second plurality of bursts may be substantially identical.

In some embodiments, the HFOs being detected may have a frequency of between about 200 Hz and about 350 Hz.

In some embodiments, the HFOs being detected may have a frequency of between about 230 Hz and about 330 Hz.

In some embodiments, the HFOs may have a frequency of between about 250 Hz and about 300 Hz.

BRIEF DESCRIPTION OF DRAWINGS

Embodiments of the present disclosure will now be described by way of non-limiting examples with reference to the drawings, in which:

FIG. 5a is a graphical illustration showing neural resonance evoked by a continuous non-therapeutic patterned DBS signal;

FIG. 5b is a graphical illustration showing neural resonance evoked by a continuous therapeutic patterned DBS signal;

FIG. 5c is a graphical illustration showing neural resonance after a transition from a continuous therapeutic DBS signal to a non-therapeutic DBS signal;

FIG. 5d is a graph illustrating the estimated frequency of evoked resonance responsive to a non-therapeutic DBS signal;

FIG. 5e is a graph illustrating the estimated frequency of evoked resonance responsive to a therapeutic DBS signal;

FIG. 5f is a graph illustrating the estimated frequency of evoked resonance responsive to a transition between a therapeutic DBS signal and a non-therapeutic DBS signal;

FIG. 6a is a graphical illustration showing neural resonance evoked by a continuous non-therapeutic patterned DBS signal;

FIG. 6b is a graphical illustration showing neural resonance evoked by a continuous therapeutic patterned DBS signal;

FIG. 6c is a graphical illustration showing neural resonance after a transition from a continuous therapeutic DBS signal to a non-therapeutic DBS signal;

FIG. 6d is a graph illustrating the estimated frequency of evoked resonance responsive to a non-therapeutic DBS signal;

FIG. 6e is a graph illustrating the estimated frequency of evoked resonance responsive to a therapeutic DBS signal;

FIG. 6f is a graph illustrating the estimated frequency of evoked resonance responsive to a transition between a therapeutic DBS signal and a non-therapeutic DBS signal;

FIG. 7a is a graph illustrating evoked resonances beginning to diverge into two peaks in response to patterned DBS with an amplitude of 1.5 mA;

FIG. 7b is a graph illustrating evoked resonances diverging into two peaks in response to patterned DBS with an amplitude of 2.25 mA;

FIG. 7c is a graph illustrating two separate evoked resonant peaks in response to patterned DBS with an amplitude of 3.375 mA;

DESCRIPTION OF EMBODIMENTS

Embodiments of the present disclosure relate to improvements in neuro-stimulation in the brain. DBS devices typically apply a constant amplitude stimulus to a target area of the brain at a constant frequency of 130 Hz. The inventors have determined not only that application of such a stimulus evokes a neural response from the target area of the brain, but that the neural response comprises a resonant component (evoked resonant neural activity (ERNA)) which has not previously been recognised. Continuous DBS at conventional frequencies does not allow a long enough time window to observe the resonant activity. However, by monitoring the neural response after stimulation has ceased (by patterning the stimulation signal or otherwise), the resonant activity can be monitored. The inventors have realised that embodiments of the present invention have applications both for reducing the physical effects associated with motor diseases, and also the detrimental effects of other neurological conditions, neuropsychiatric disorders, sensory disorders, and pain. FIGS. 1 to 7c illustrate the effects of patterned and non-patterned stimuli on measured ERNA.

Figure 1:
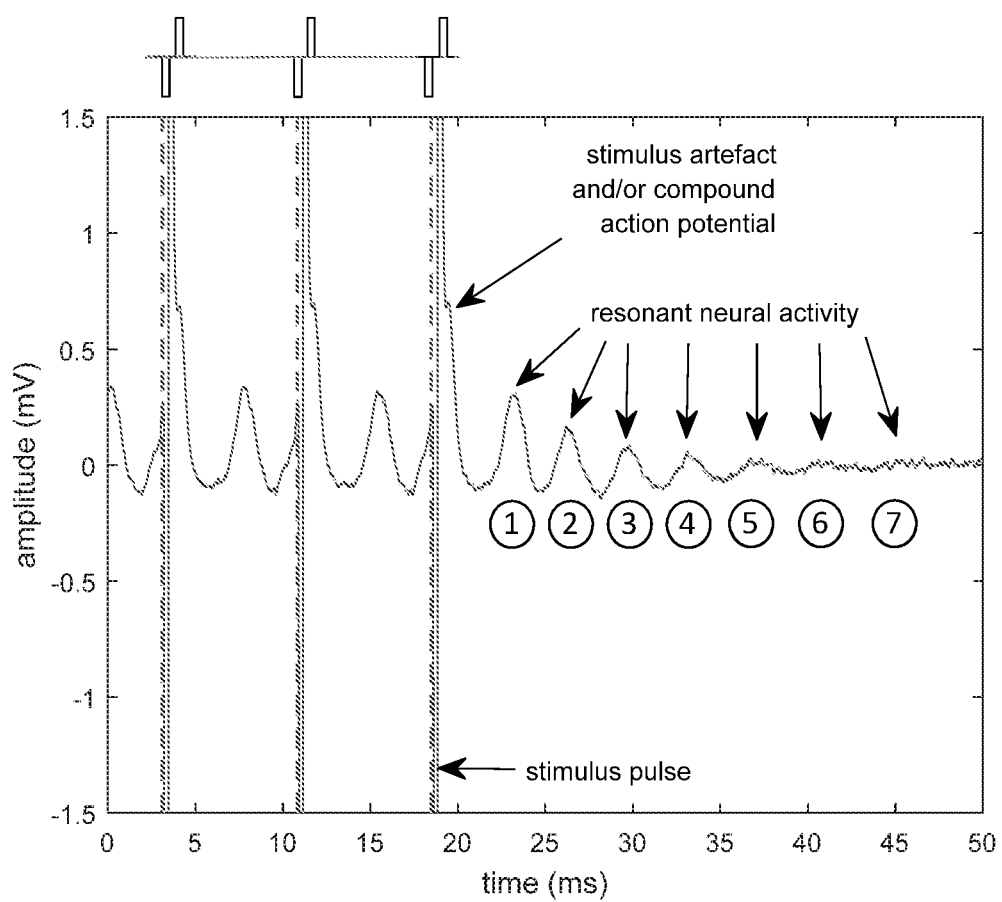
FIG. 1 is a graph illustrating resonance from a neural structure responsive to a deep brain stimulation (DBS) signal.

In addition to the above, the inventors have realised that neuronal oscillations, as reflected in local field potentials measured by EEG and MEG signals, are also affected by DBS. In particular, the inventors have found that high frequency neural oscillations (HFOs) in the range of 200 to 500 Hz, measured in local field potentials by DBS electrodes implanted in the brain, appear to be affected by DBS. This realisation has led the inventors to develop novel techniques of selecting optimal DBS treatment parameters based on characteristics of measured HFOs. FIG. 1 graphically illustrates a response from a neural circuit stimulated by a 130 Hz signal delivered from a neurostimulator via an electrode lead, such as the 3387 electrode lead manufactured by Medtronic®, implanted in the subthalamic nucleus (STN) of a Parkinson's disease (PD) patient. Each response to a stimulus pulse comprises an evoked compound action potential (ECAP) component together with a component of evoked resonant neural activity (ERNA) occurring after the ECAP. The ECAP typically occurs within 1-2 milliseconds of the stimulus pulse. The graph shows the response to the last three consecutive pulses of a 60 second period of continuous stimulation followed by a period of no stimulation. It can be seen that the evoked resonant response to each of the first two stimulus pulses shown in FIG. 1 is cut short by the onset of the next stimulus pulse, such that only a single secondary peak is detected. However, the evoked resonant response to the third (and final) pulse is able to resonate for longer and so can be clearly seen in the form of a decaying oscillation with at least seven peaks for a post-stimulus period of about 30 milliseconds.

As mentioned above, it is known for clinicians to control and adjust DBS parameters to elicit therapeutic effects in a patient. The inventors have realised that by controlling the DBS parameters in certain ways, a non-therapeutic stimulus can be administered which evokes a resonant neural response (ERNA) in a patient without having any therapeutic impact or causing undesirable side effects. Such non-therapeutic stimuli can be used to reliably measure ERNA without causing sustained changes to the resonant neural circuit or the patient's symptomatic state. Non-therapeutic stimulation is preferably achieved by administering a stimulus comprising a short burst of pulses followed by a period of no stimulation, and the ERNA is measured during this period of no stimulation. By doing so, the total charge or energy provided to the patient is below a therapeutic threshold, and the measured ERNA provides information concerning the patient's natural state (without therapy). In an alternative embodiment, the overall charge or energy provided to the patient may be reduced by reducing the amplitude of the stimulation signal below a therapeutic threshold. However, doing so may also reduce the amplitude of peaks in the ERNA making it more difficult to observe.

In addition to the above, the inventors have determined that patterned stimulation can be used to monitor and analyse evoked resonant neural activity during therapeutic stimulation of a patient. By patterning the stimulation signal, therapeutic stimulation can be maintained whilst providing time windows in which to monitor resonant responses past that of the first resonant peak or more preferably past two or more resonant peaks.

Figure 2:
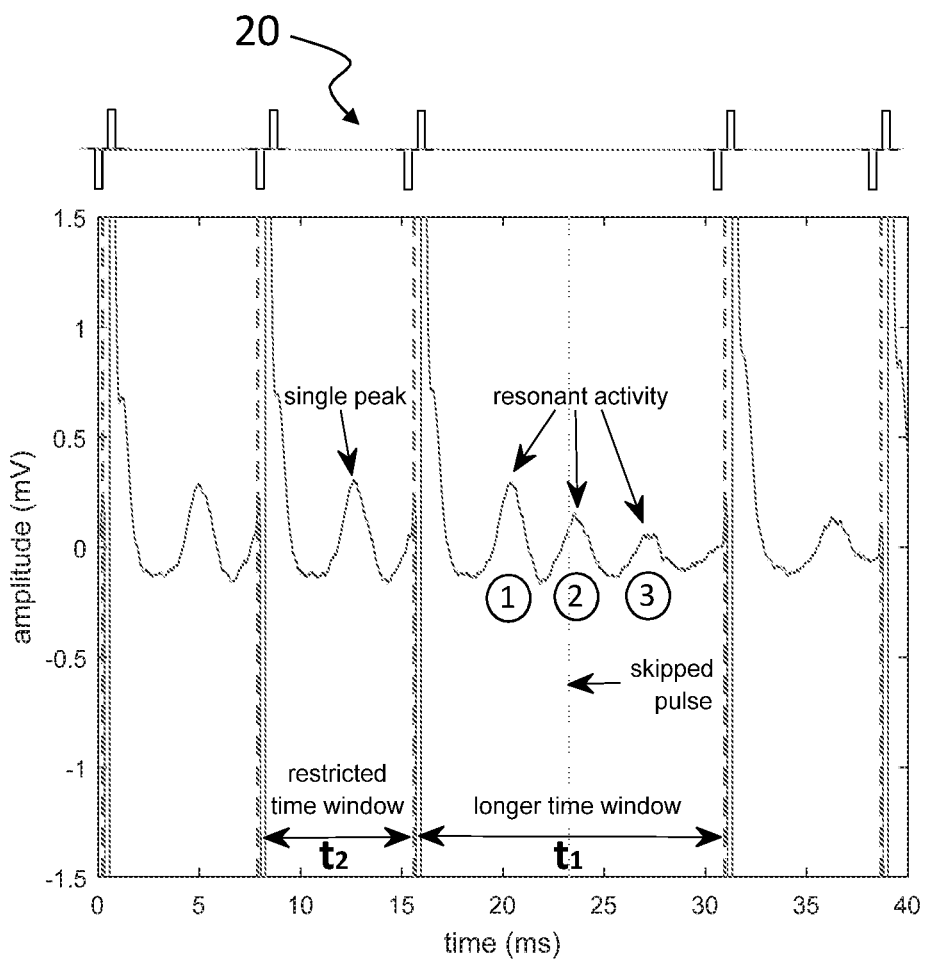
FIG. 2 is a graph illustrating resonance from a neural structure responsive to a patterned DBS signal.

FIG. 2 graphically illustrates an example therapeutic patterned DBS stimulus 20 and the associated evoked resonant response according to an embodiment of the present disclosure. The patterned stimulus 20 is shown above the graph to illustrate the correlation between stimulus and response. In the patterned stimulus, a single pulse has been omitted from an otherwise continuous 130 Hz pulse train. The pulse train therefore includes a plurality of bursts of pulses of continuous stimulation, each burst separated by a first time period $t_1$, each of the plurality of pulses separated by a second time period $t_2$. Continuation of the stimulus before and after omission of a pulse (or more than one pulse) maintains the therapeutic nature of the DBS, whilst the omission of a pulse allows for resonance of the ERNA to be monitored over several (3 in this example) resonant cycles before the next stimulation pulse interrupts this resonance.

In summary, by patterning non-therapeutic and therapeutic stimuli, an evoked response can be monitored over a longer period of time than with conventional non-patterned stimulation. Accordingly, stimuli are preferably applied in bursts of multiple pulses, each burst separated by a first time period $t_1$ of no stimulation, each pulse separated by a second time period $t_2$. For example, a stimulus signal may comprise a series of 10-pulse bursts at 130 Hz. To increase repeatability of results, the multi-pulse burst may be repeated after a predetermined period of no stimulation. For example, the multi-pulse burst may be repeated each second. The duration of the first time period $t_1$ is greater than that of the second time period $t_2$. The ratio between the duration of the burst and the duration between bursts may be chosen so as to ensure that relevant properties of the ERNA can be monitored easily and efficiently. In some embodiments, the duration of each burst is chosen to be between 1% and 20% of the duration of no stimulation between bursts.

Figure 3:
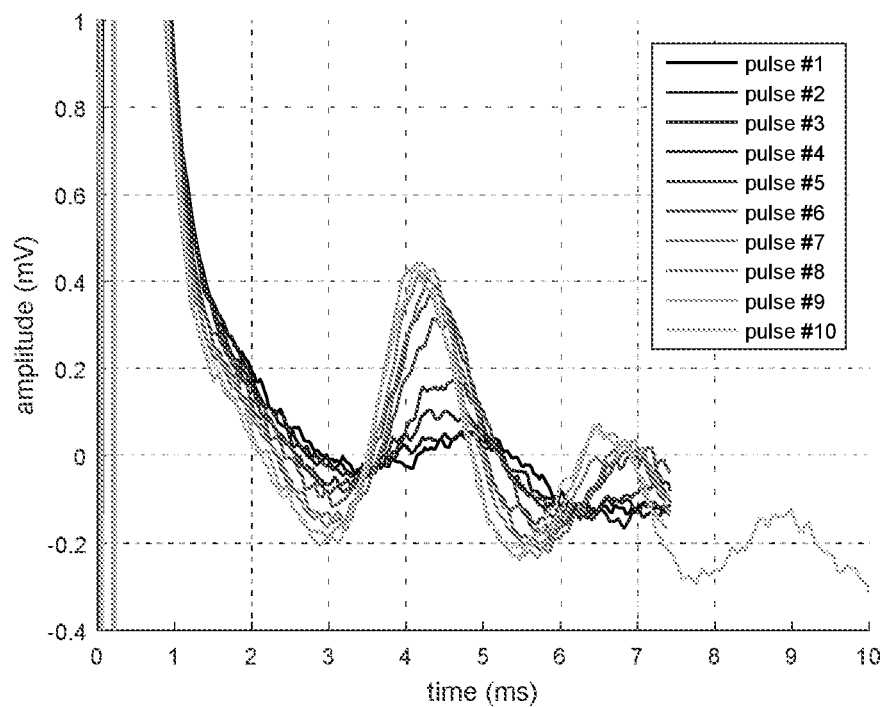
FIG. 3 is a graph illustrating evoked resonance responsive to 10 consecutive pulses of a DBS signal.

In other embodiments, the duration of each burst may be chosen to minimise the effects of stimulation on the measured ERNA or to accentuate particular features of the measured ERNA. FIG. 3 graphically illustrates how the application of 10 pulses at 130 Hz can affect ERNA. The response to the first pulse has a broad, low amplitude first peak. The first peak becomes larger and sharper for subsequent pulses, whilst also shifting to an earlier time. In some embodiments, the optimum number of pulses comprised in a burst may be chosen to maximise the amplitude of the resonance, whilst minimizing the time shift of a peak in ERNA across the burst (e.g., the fourth pulse). In other embodiments, the rate of change in ERNA features (e.g. amplitude, onset delay) across consecutive pulses in a burst may be used as a defining characteristic. For example the rate of change across a burst may be used to determine electrode position, optimum parameters, patient state, etc. and/or as a closed loop control signal.

Figure 4:
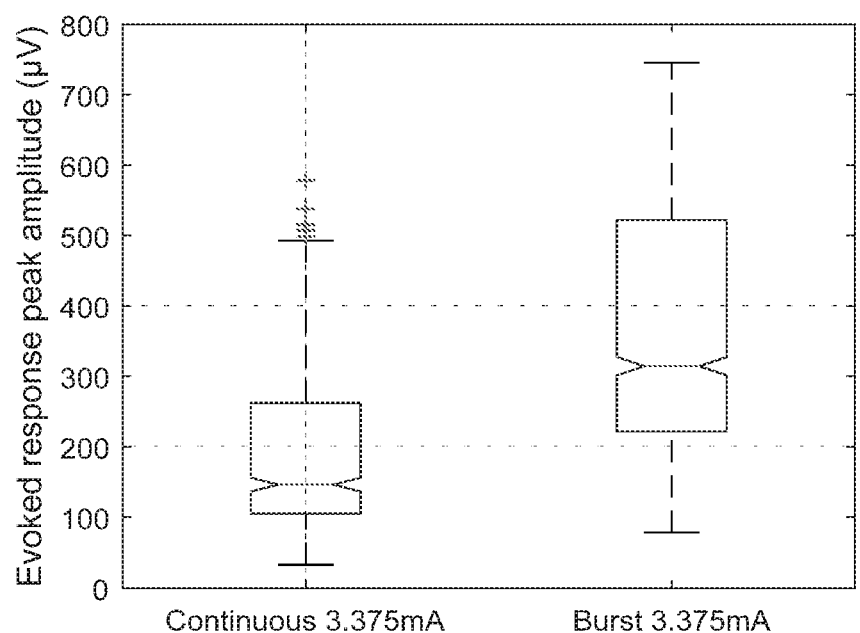
FIG. 4 is a graph illustrating the range and variance of peak amplitude of a resonant response to continuous and patterned DBS.
Figure 8:
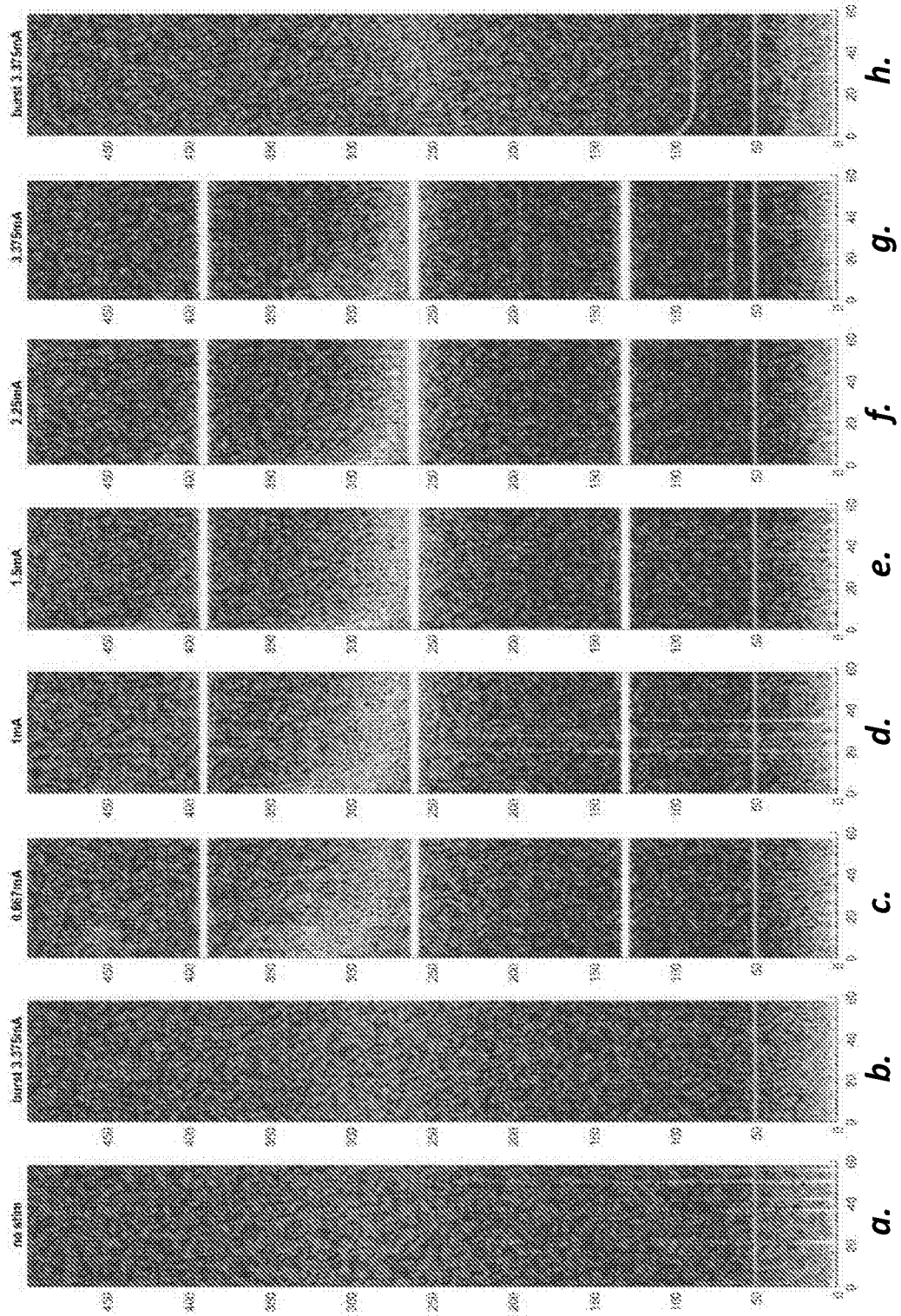
FIGS. 8a to 8h are spectrograms of high frequency oscillations recorded in a brain during deep brain stimulation.
Figure 9:
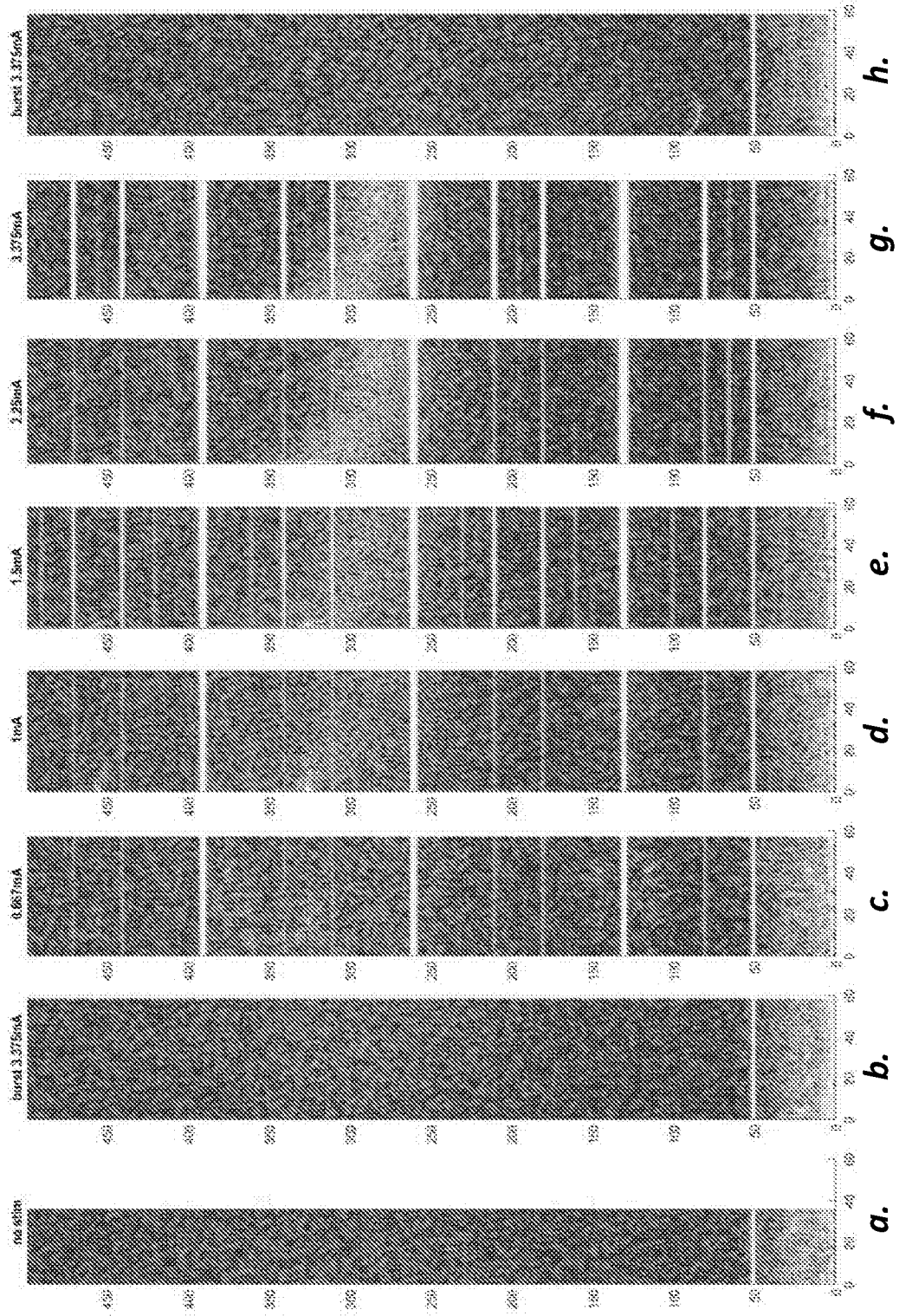
FIGS. 9a to 9h are spectrograms of high frequency oscillations recorded in a brain during deep brain stimulation.
Figure 10:
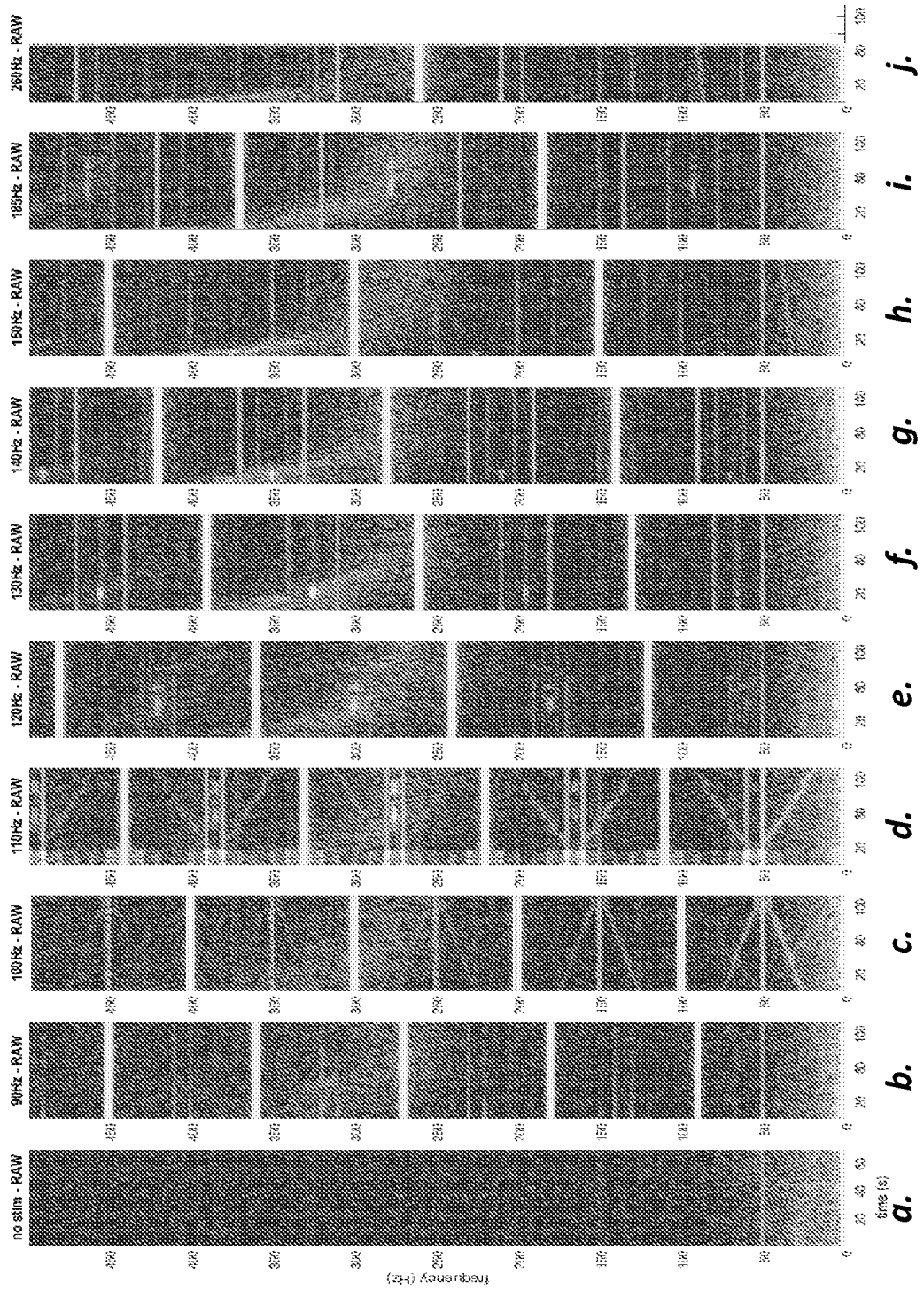
FIGS. 10a to 10h are spectrograms of high frequency oscillations recorded in a brain during deep brain stimulation.

The use of burst (e.g. 10 pulses) stimulation provides high amplitude evoked neural responses, making them easier to measure than responses to more continuous DBS. FIG. 4 graphically illustrates the range and variance of first peak amplitude of ERNA responsive to more continuous DBS where one pulse is skipped every second (left) and burst DBS (right) (10 pulses only per second). It can be seen that the average peak amplitude of ERNA responsive to burst DBS is around 310 µV whereas the average peak amplitude of ERNA responsive to more continuous DBS is around 140 µV. Further, by using burst stimulation, the evoked resonant response over several oscillatory cycles (20 milliseconds or more) can be monitored.

By analysing characteristics of the ERNA, the inventors have determined that waveform characteristics of the ERNA (natural frequency, damping factor, envelope, fine structure, onset delay, rate of change, etc.) are dependent on various physiological conditions of the patient. For example, it has been found that therapeutic DBS decreases the frequency of resonance of the target neural circuit.

FIGS. 5a, 5b, and 5c illustrate the variation of frequency of the ERNA during non-therapeutic stimulation (FIG. 5a), therapeutic stimulation (FIG. 5b), and the ERNA after a transition of stimulation from therapeutic stimulation to non-therapeutic stimulation (FIG. 5c). Resonant frequency of the ERNA was measured by calculating the inverse of the time delay between the maxima of two peaks of the ERNA. In other embodiments, the resonant frequency may be calculated as an inverse of the average time delay between maxima of all detected peaks of the ERNA. In further embodiments, the resonant frequency may be calculated by fitting a damped oscillator model to the resonant activity and extracting the natural frequency or by performing spectral analyses (e.g. Fourier transform, wavelet transform). Other techniques for frequency estimation, such as estimating the time between zero-crossings in the waveform or using other features of the waveform may also be used for this purpose.

In the example shown, a patterned stimulus was administered to the patient in the same manner as described with reference to FIGS. 1 and 2. FIGS. 5a and 5b show the responses to a patterned non-therapeutic and therapeutic DBS stimulation, respectively. In this example, non-therapeutic stimulation consisted of bursts of 10 pulses delivered at a frequency of 130 Hz over a 1-second time period with the remaining 120 pulses (which would be present during continuous stimulation) skipped. The typical observable window of the response (during continuous (non-patterned) DBS) is denoted by the horizontal dotted line. It can be seen that with patterned non-therapeutic stimulation, the amplitude and frequency of the ERNA remain relatively constant indicating that the stimulus did not strongly affect the resonant state of the target neural structure over time. Further, two resonant peaks of the ERNA (represented in black) can be seen in the typical observable window for non-patterned stimulation. FIG. 5b then shows the responses to therapeutic patterned DBS stimulation at 3.375 mA where 129 pulses are delivered per second at a rate of 130 Hz, with the remaining 1 pulse skipped.

The therapeutic signal causes the frequency of the ERNA to reduce, in turn potentially causing the second resonant peak of the ERNA to move outside the typical observable window for continuous (non-patterned) stimulation. However by patterning the stimulation by skipping one or more pulses, it is possible to continue to measure the resonant properties of the ERNA, along with subsequent peaks during the period in which a stimulation pulse is omitted. Additionally, it can be seen that the amplitude of the third and fourth resonant peaks are increased in comparison to the non-therapeutic responses.

Alternative methods of patterning the stimulation, rather than merely omitting pulses in a periodic pulse train, may improve the monitoring of ERNA. For example, the amplitude of pulses may be modulated over time, including applying a ramp to increase the pulse amplitudes over several pulses within a burst and/or a ramp to decrease the pulse amplitudes over several pulses within a burst. To enhance the monitoring of ERNA it may be advantageous to apply a fixed amplitude to the pulses preceding the observation window, and if this amplitude differs from that applied at other times (e.g. to maximise therapeutic benefit), then applying ramps to the amplitude of the pulses to avoid an abrupt step change in amplitude may be advantageous.

FIG. 5c then shows the responses after switching back to the non-therapeutic patterned stimulation. In this case the therapeutic effect of the patterned therapeutic stimulus 'washes out' and the ERNA returns to its baseline state. It can be seen that the first peak of resonant activity across all conditions (typically all that can be measured using conventional continuous DBS) does not vary greatly with therapeutic DBS. However, characteristics of subsequent parts of the ERNA waveform, made measurable by patterning the stimulation, exhibit much larger changes in frequency and amplitude. Monitoring of the response over a longer period therefore enables information concerning frequency, amplitude, envelope, and fine structure of the time-varying oscillation to be analysed.

This effect is further illustrated by FIGS. 5d, 5e, and 5f. FIG. 5d shows the resonant frequency of the ERNA during periods of non-therapeutic stimulation to be around 400-450 Hz. Clinically effective stimulation (stimulation operable to actively reduce a patient's disease symptoms) reduces the frequency of the ERNA to around 300-350 Hz as shown in FIG. 5e. FIG. 5f illustrates the transition of resonant frequency from 300-350 Hz back to around 400-450 Hz after therapeutic stimulation has been replaced with non-therapeutic stimulation.

FIGS. 6a, 6b, and 6c illustrate another example from a different patient of the variation of the ERNA during non-therapeutic patterned stimulation (FIG. 6a), therapeutic patterned stimulation (FIG. 6b) and the ERNA after a transition from therapeutic stimulation to non-therapeutic stimulation (FIG. 6c). In this example, patterned stimuli were administered to the patient in the same manner as described with reference to FIGS. 5a to 5e. As with the previous example, it can be seen that the initial non-therapeutic stimulation (FIG. 6a) does not cause noticeable changes to the ERNA and that the therapeutic stimulation (FIG. 6b) causes a reduction in the frequency of the resonance, which returns to baseline levels after the stimuli is transitioned back to non-therapeutic patterned stimulation (FIG. 6c). However, in this example, the change in resonant frequency with therapeutic stimulation is accompanied by an increase in the delay between each stimulus pulse and the onset of the resonance. This increase in onset delay shifts the second resonant peak such that it occurs outside the typical observable window for conventional (non-patterned) DBS. By patterning the stimulation, the measurement window is made long enough to observe three resonant peaks, allowing ERNA to be characterised. Furthermore, contrary to the previous example, the amplitude of the resonance is decreased by therapeutic stimulation.

FIGS. 6d, 6e, and 6f further illustrate the reduction in resonant frequency with therapeutic stimulation in this example. Resonant frequency was estimated by calculating the inverse of the time delay between the maxima of two peaks of the ERNA. In FIG. 6d, the frequency of the ERNA measured using non-therapeutic patterned stimulation can be seen to be about 350 Hz. The application of therapeutic patterned stimulation in FIG. 6e causes the frequency to decrease to around 250 Hz. The frequency can be seen to be returning to its baseline level in FIG. 6f after transitioning back to non-therapeutic patterned stimulation.

The inventors have determined not only that evoked neural responses to applied stimuli exhibit resonant activity, but that in some instances evoked activity comprises multiple resonances. FIGS. 7a, 7b and 7c illustrate ERNA in response to continuous DBS at 1.5 mA, 2.25 mA and 3.375 mA respectively. At 1.5 mA the resonant ERNA starts as a single peak, which can be seen to begin to diverge slightly into two peaks. At 2.25 mA, the dominance switches to the later of the two peaks. However, the earlier peak, which was dominant at 1.5 mA, continues at a lower amplitude. At 3.375 mA, two peaks are present, with the later peak dominating. It is thought that these multiple resonant peaks correspond to activity in different neural circuits. The relative amplitude between these resonant responses (or other features, such as temporal or spectral properties) may be an indicator of therapeutic state.

The identification of a correlation between changes in resonant behaviour of stimulated neural circuits and a patient's disease symptoms present several opportunities to improve aspects of DBS therapy, including but not limited to techniques for initial implantation and subsequent repositioning of DBS electrodes, together with techniques for setting parameters of DBS stimulation and using feedback to adjust DBS parameters in real time whilst DBS therapy is underway.

The preceding paragraphs provide an analysis of the relationship between DBS and evoked resonant neural activity, i.e. resonant responses evoked by DBS. The inventors have also realised, however, that DBS can affect spontaneous neuronal activity in the brain, in particular high frequency oscillations (HFOs) which can be measured in local field potentials (LFPs).

Previous attempts to monitor HFOs during DBS stimulation have proven difficult. Due to the relatively low quality of recording equipment, artefacts have up until now been in recordings of local field potentials which result from stimulation. As a result, HFOs have not previously been characterised during deep brain stimulation, nor used in the treatment of motor diseases.

The inventors have realised that artefacts in recorded local field potentials can be reduced by manipulating characteristics of the DBS stimulation waveform without affecting patient therapy administered using DBS. In particular, it has been found that during recording of local field potentials, charge associated with the longer duration low-amplitude portion of an asymmetric stimulus couples to the apparatus used to process electrical signals received from recording electrodes. In particular, this charge coupling causes recording amplifier(s) to operate in a non-linear state, which results in inaccurate measurements and the aforementioned artefacts.

The inventors have found that by using a symmetric DBS stimulus, they are able to reduce instances of charge coupling so as to increase the visibility of HFOs in local field potentials. Whilst less ideal, a similar affect may also be achieved by using a biphasic stimulation waveform having a first phase at a first amplitude for a first duration and a second phase of opposite polarity to the first phase, the second phase having a second amplitude and a second duration, the product of the first amplitude and the first duration being substantially equal to the product of the second amplitude and the second duration. In doing so, the charge of the first and second phases of the waveform are equal and opposite. In one embodiment, a biphasic stimulation waveform may be used in which the second phase was half the amplitude and double the duration of the first phase. In another embodiment, a biphasic stimulation waveform may be used in which the second phase was a third the amplitude and triple the duration of the first phase.

In addition and as described in more detail below, patterned DBS stimulation can be used to enhance the visibility of HFOs so that they can be used to set DBS stimulation parameters, guide the placement of DBS electrodes, track therapy and disease progression, and help with control of closed loops DBS stimulation.

Using novel DBS stimulation techniques, accurate recordings of HFOs have been acquired. By analysing characteristics of the HFOs, the inventors have determined that waveform characteristics of the HFOs (such as natural frequency, bandwidth, amplitude, rate of change of frequency and/or amplitude, etc.) are dependent on various physiological conditions of the patient. For example, it has been found that therapeutic DBS causes HFO activity in the brain to tend toward a particular, patient-specific frequency. It has also been found that the frequency to which HFO is driven by DBS is independent of the frequency of the DBS stimulation waveform. In fact, it has been found that DBS stimuli having different frequencies, when applied to the brain of a common patient, result in HFO activity being driven to the same frequency, suggesting that there is an inherent frequency at which the aggregate neuronal brain activity of a patient oscillates after application of DBS for a period of time. This frequency to which HFO activity trends will herein by referred to as the HFO characteristic frequency.

FIGS. 8a to 8h illustrate this activity by way of a series of spectrograms which show the effect of varying DBS stimulus amplitude on measured HFO frequency.

A patient was stimulated by a 130 Hz pulse train comprising biphasic symmetric pulse waveforms delivered from a neurostimulator via an electrode lead, such as the 3387 electrode lead manufactured by Medtronic®, implanted in the subthalamic nucleus (STN) of the patient. The pulse width was 60 μs per phase. The amplitude of the stimulus was varied in a stepwise manner between 0 A and 3.375 mA as denoted at the top of each spectrogram. A very short gap in stimulation (period of zero stimulation) of approximately 1 second was present in the stimulus between each amplitude condition. On each spectrogram, the vertical axis corresponds to frequency in hertz and the horizontal axis corresponds to time in seconds. Measured local field potentials, which include HFOs, are depicted in lighter shades in each spectrogram. The whiter the shade, the stronger the signal received at electrodes at a particular frequency and time.

FIG. 8a is a spectrogram showing measured local field potentials during periods of zero stimulation (HFO activity across a frequency range in hertz over time in seconds. FIGS. 8b and 8h are spectrograms showing HFO activity during non-therapeutic patterned DBS. FIGS. 8c to 8g are spectrograms showing HFO activity during therapeutic DBS.

It can be seen that during periods of no stimulation (shown in FIG. 8a) and during periods of non-therapeutic stimulation (shown in FIGS. 8b & 8h), a very faint area of HFO activity was recorded as shown in the respective spectrograms. This activity is spread over a frequency range approximately between 230 Hz and 330 Hz.

With the onset of therapeutic DBS at 0.667 mA a much stronger recording of HFO activity is acquired as shown in FIG. 8c, suggesting that the application of DBS at certain frequencies (in this case 130 Hz) increases the visibility of HFOs in recorded local field potentials. Moreover, the application of therapeutic DBS at 0.667 mA causes a downward trend of HFO frequency over time which plateaus at around 260 Hz to 270 Hz after 30 s. It has been found that this plateau in HFO activity frequency (the HFO characteristic frequency) correlates with a reduction in disease-related physical effects associated with motor disease in a patient.

The reduction of HFO frequency over time is also observed during application of DBS having amplitudes of 1 mA, 1.5 mA, 2.25 mA, and 3.375 mA as shown in FIGS. 8*d*, 8*e*, 8*f* and 8*g* in which the frequency of HFO activity is seen to decrease to approximately the same HFO characteristic frequency of around 260 Hz.

The spectrograms of FIGS. 8*c* to 8*g* also show that the rate of change of frequency of recorded HFO activity increases with increasing amplitude, suggesting that higher amplitude DBS causes HFO activity to reach its final frequency more quickly. However, FIG. 8*g* shows that when DBS amplitude increases beyond a threshold, HFO activity is suppressed when compared with HFO activity at lower DBS amplitudes (e.g. FIGS. 8*c* and 8*d*). This is exemplified in FIG. 8*g*, which shows that HFO activity during stimulation at 3.375 mA reduces visibility of HFO activity.

This data can be used to identify optimal stimulation amplitudes for therapy. For example, the amplitude can be chosen to be high enough to steady HFOs at the HFO characteristic frequency but not so as high as to suppress HFOs.

It is noted that the above measured HFO characteristic frequency of 260 Hz is a harmonic (×2) of the default DBS rate (130 Hz) that has been found to be effective in a large proportion of patients undergoing conventional DBS therapy. It is noted, however, that the default 130 Hz DBS rate is not the optimum stimulation rate for all patients undergoing DBS therapy. In some instances, DBS therapy at 130 Hz is, in fact, detrimental. The inventors have realised that this is likely due to a variation of HFO characteristic frequency between patients. For example, whilst a large proportion of patients may exhibit an HFO characteristic frequency of around 260 Hz, some patients may exhibit a different HFO characteristic frequency indicating that a different DBS rate would be more effective in their therapy. Accordingly, measurements of HFOs taken in accordance with FIGS. 8*a* to 8*g* may be used to identify a characteristic frequency associated with a patient, which in turn may be used to determine an optimum frequency for DBS therapy.

Having regard for the above, FIGS. 9*a* to 9*h*, which depict HFO activity across a frequency range (in Hz) over time (in seconds), provide a further example of the effect of DBS amplitude on HFO activity in a different patient. In this example, in the presence of DBS at 130 Hz, HFO activity is driven to a HFO characteristic frequency of around 280 Hz which is different to the HFO characteristic frequency of the patient whose HFO activity is shown in FIGS. 8*a* to 8*h*. Through analysis of HFO activity of several patients, it has been found that the HFO characteristic frequency to which HFO activity trends during therapeutic DBS is patient specific and can vary widely (typically between 200 Hz and 350 Hz). As previously stated, this suggests that there is a patient specific frequency at which the aggregate neuronal brain activity of a patient oscillates during DBS and that it may be preferable to adjust DBS rate to correlate with this HFO characteristic frequency. Accordingly, HFO activity can also be used to identify optimum stimulation frequencies for therapy.

It has also been discovered that the HFO characteristic frequency is independent of DBS stimulation frequency. FIGS. 10*a* to 10*j* are spectrograms of HFOs measured in local field activity for a patient being administered with DBS at varying frequencies of stimulation (zero stimulation in the case of FIG. 10*a*). These results are taken from measurements of a different patient to those of FIGS. 8 and 9. For each frequency of stimulation, it can be seen that at the onset of stimulation, HFO activity is centred at a different frequency which seems to be related approximately to the frequency of DBS. However, after a period of time (within approx. 100 s) in each case the frequency of HFO activity tends to the same HFO characteristic frequency; around 260 Hz. The most effective DBS rate for therapeutic treatment of the patient to which FIGS. 10*a* to 10*j* relate was found to be 130 Hz, which again is half of the measured HFO characteristic frequency. This again suggests that the HFO characteristic frequency of a patient relates to the most effective DBS frequency for patient therapy.

A number of practical applications of the above described evoked resonant neural activity and HFO activity will now be discussed with reference to several embodiments. In the embodiments, one or more electrode leads may be used for stimulation of one or more neural structures within one or both hemispheres of the brain, each lead comprising one or more electrodes located near the tip of each lead. Each of the electrodes may be used for stimulation, monitoring, or both stimulation and monitoring. One or more of these electrodes may be implanted. Implanted electrodes may be used independently or in addition to one or more electrodes placed on the outside of the brain or skull.

Figure 11:
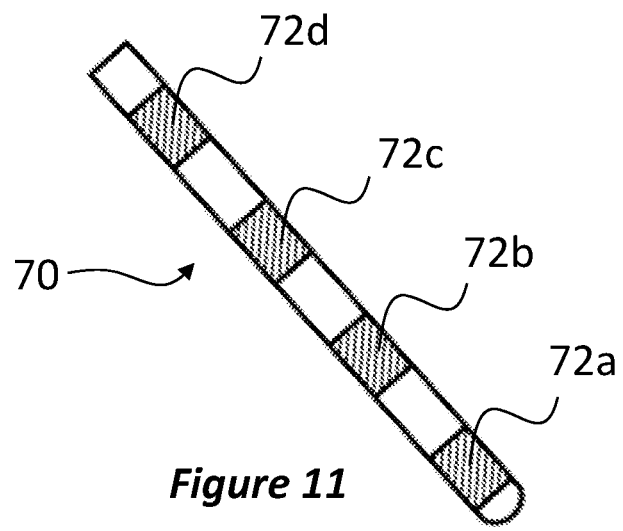
FIG. 11 is a schematic illustration of an electrode lead tip for implantation in a brain.

A typical DBS electrode lead tip 70, such as that incorporated into the Medtronic® DBS Lead Model 3387, is shown in FIG. 11. The lead tip 70 comprises a first electrode 72*a*, a second electrode 72*b*, a third electrode 72*c*, and a fourth electrode 72*d*. Once implanted into the brain, each of the electrodes 72*a*, 72*b*, 72*c*, 72*d* may be used to apply a stimulus to one or more neural structures or monitor and optionally record the evoked response (including ERNA) from neural circuits to the stimulus and the HFO activity measured from local field potentials in the brain. In other embodiments, leads with more electrodes or electrodes with different sizes or topologies may be used. In addition, one or more reference electrodes may be located at a remote site and used to complete the electrical circuit when one or more electrodes on the DBS lead are activated for stimulation or used for signal monitoring.

The target location for the lead tip 70 varies dependent on the neural structure. Example target structures include but are not limited to the subthalamic nucleus (STN), the substantia nigra pars reticulata (SNr), and the globus pallidus interna (GPi).

Figure 12:
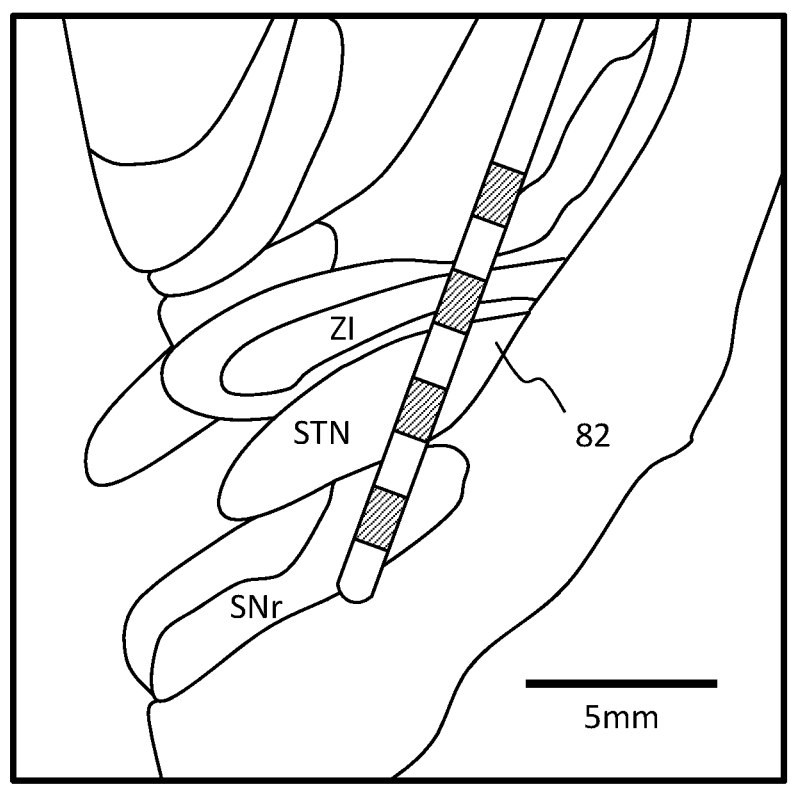
FIG. 12 is a schematic illustration of an electrode lead implanted in the subthalamic nucleus of a brain.

FIG. 12 shows the lead tip 70 implanted into a brain at a target structure, in this case the subthalamic nucleus (STN) 82. It will be appreciated that intersecting the electrode tip 70 with the subthalamic nucleus (STN) 82, which has a typical diameter of 5 to 6 mm, can be a very difficult surgical task. Techniques such as stereotactic imaging, microelectrode recordings, intraoperative x-ray imaging, and applying therapeutic stimulation whilst monitoring patient symptoms, are currently used to localise the electrode tip 70. However, these methods can lack accuracy. Additionally, existing methods usually require the patient to be awake for the procedure, since voluntary responses from the patient can be used to confirm that the electrode is at a suitable location relative to a target structure in the brain. For this reason, many potential recipients of DBS therapy turn down the option because they are not comfortable with having to be awake during the surgical procedure.

The accuracy of locating electrodes of the electrode tip 70 within a target structure can be greatly increased by using a series of patterned stimulations to generate and measure an evoked resonant response from a neural target. Such techniques can obviate the need for the patient to be awake during the implantation procedure, since an electrode can be located much more accurately at the correct location within the brain and relative to a target neural structure. This means that patients can be under sedation or general anaesthetic during the surgery since no patient feedback is required to locate the electrode to a satisfactory degree of accuracy.

Figure 13:
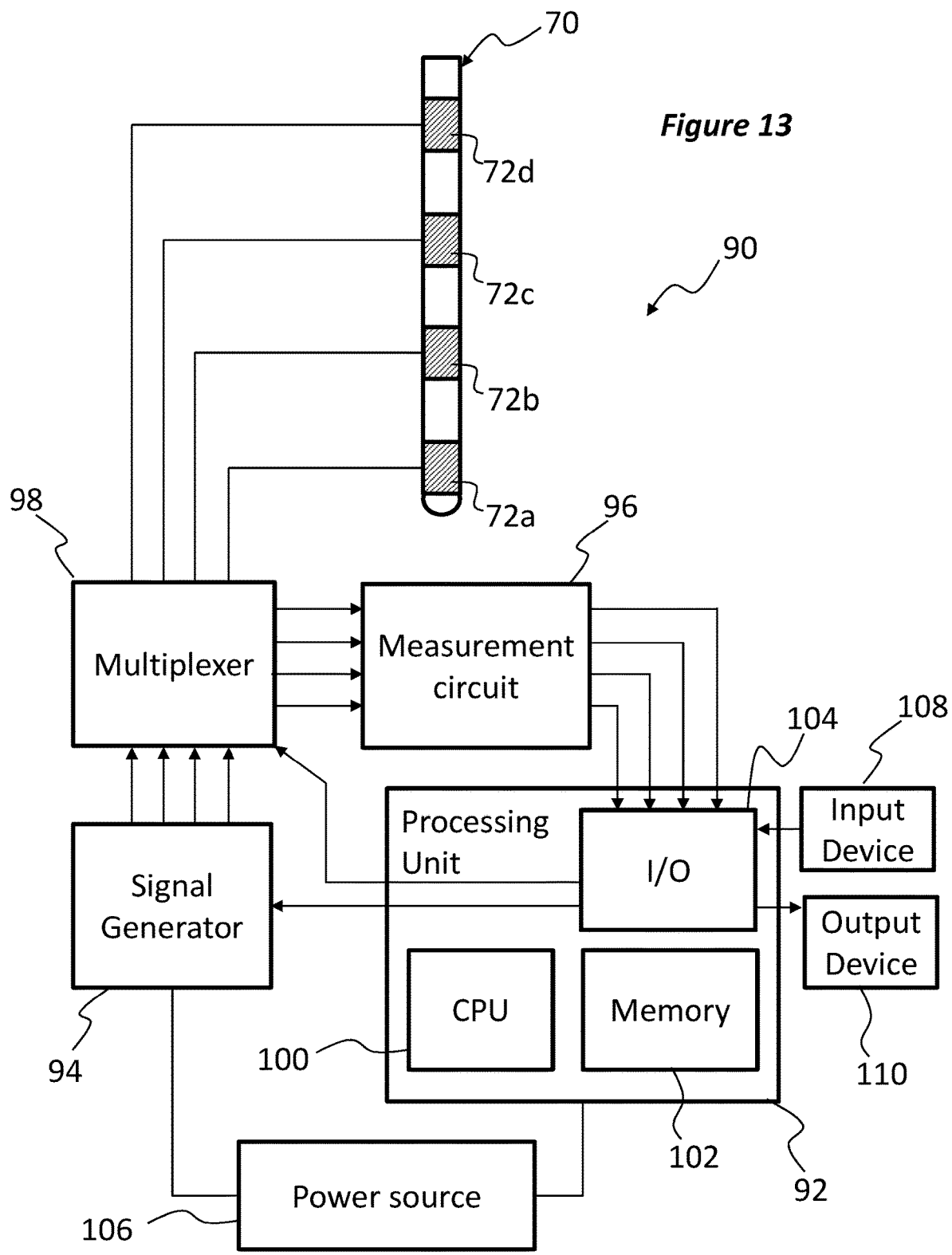
FIG. 13 is a schematic illustration of a system for administering DBS.

An example DBS delivery system 90 according to an embodiment of the present disclosure is illustrated in FIG. 13. The system 90 comprises the lead tip 70 of FIG. 11 including the plurality of integrated electrodes 72a, 72b, 72c, 72d, together with a processing unit 92, a signal generator 94, a measurement circuit 96 and an optional multiplexer 98. The processing unit comprises a central processing unit (CPU) 100, memory 102, and an input/output (I/O) bus 104 communicatively coupled with one or more of the CPU 100 and memory 102.

In some embodiments, the multiplexer 98 is provided to control whether the electrodes 72a, 72b, 72c, 72d are connected to the signal generator 94 and/or to the measurement circuit 96. In other embodiments the multiplexer may not be required. For example, the electrodes 72a, 72b, 72c, 72d may instead be connected directly to both the signal generator 94 and the measurement circuit 96. Although in FIG. 13 all of the electrodes 72a, 72b, 72c, 72d are connected to the multiplexer 98, in other embodiments, only one or some of the electrodes 72a, 72b, 72c, 72d may be connected.

The measurement circuit 96 may include one or more amplifiers and digital signal processing circuitry including but not limited to sampling circuits for measuring neural responses to stimulation, including ERNA. In some embodiments the measurement circuit 96 may also be configured to extract other information from received signals, including local field potentials for measurement of HFOs and the like. The measurement circuit 96 may also be used in conjunction with the signal generator 94 to measure electrode impedances. The measurement circuit 96 may be external to or integrated within the processing unit 92. Communication between the measurement circuit 96 and/or the signal generator 94 on the one hand and the I/O port on the other may be wired or may be via a wireless link, such as over inductive coupling, WiFi®, Bluetooth® or the like. Power may be supplied to the system 90 via at least one power source 106. The power source 106 may comprise a battery such that elements of the system 90 can maintain power when implanted into a patient.

The signal generator 94 is coupled via the multiplexer 98 to one or more of the electrodes 72a, 72b, 72c, 72d and is operable to deliver electrical stimuli to respective electrodes based on signals received from the processing unit 92. To this end, the signal generator 94, the multiplexer 98 and the processing unit 92 are also communicatively coupled such that information can be transferred therebetween.

Whilst the signal generator 94, multiplexer 98, and the processing unit 92 in FIG. 13 are shown as separate units, in other embodiments the signal generator 94 and multiplexer may be integrated into the processing unit 92. Furthermore, either unit may be implanted or located outside the patient's body.

The system 90 may further comprise one or more input devices 108 and one or more output devices 110. Input devices 108 may include but are not limited to one or more of a keyboard, mouse, touchpad and touchscreen. Examples of output devices include displays, touchscreens, light indicators (LEDs), sound generators and haptic generators. Input and/or output devices 108, 110 may be configured to provide feedback (e.g. visual, auditory or haptic feedback) to a user related, for example, to characteristics of ERNA or subsequently derived indicators (such as proximity of the electrode 70 relative to neural structures in the brain. To this end, one or more of the input devices 108 may also be an output device 110, e.g. a touchscreen or haptic joystick. Input and output devices 108, 110 may also be wired or wirelessly connected to the processing unit 92. Input and output devices 108, 110 may be configured to provide the patient with control of the device (i.e. a patient controller) or to allow clinicians to program stimulation settings, and receive feedback of the effects of stimulation parameters on ERNA and/or HFO characteristics.

One or more elements of the system 90 may be portable. One or more elements may be implantable into the patient. In some embodiments, for example, the signal generator 94 and lead 70 may be implantable into the patient and the processing unit 92 may be external to the patient's skin and may be configured for wireless communication with the signal generator via RF transmission (e.g. induction, Bluetooth (®), etc.). In other embodiments, the processing unit 92, signal generator 94 and lead 70 may all be implanted within the patient's body. In any case, the signal generator 94 and/or the processing unit 92 may be configured to wirelessly communicate with a controller (not shown) located external to the patient's body.

One embodiment of the present disclosure provides a system and method for localising the lead tip 70 within a target structure of the brain using measured ERNA and/or HFO activity. During an operation for implantation of the lead tip 70 into the brain, instead of relying on low accuracy positioning techniques as described above to estimate the location of electrodes relative to neural structures within the brain, the system 90 may be used to provide real-time feedback to the surgeon based on characteristics such as the strength and quality of evoked response signals received from one or more electrodes of the lead tip 70. This feedback may be used to estimate position within the target structure in three dimensions and to inform the decision of whether to reposition the electrodes or remove and reimplant the electrodes along a different trajectory.

Figure 14:
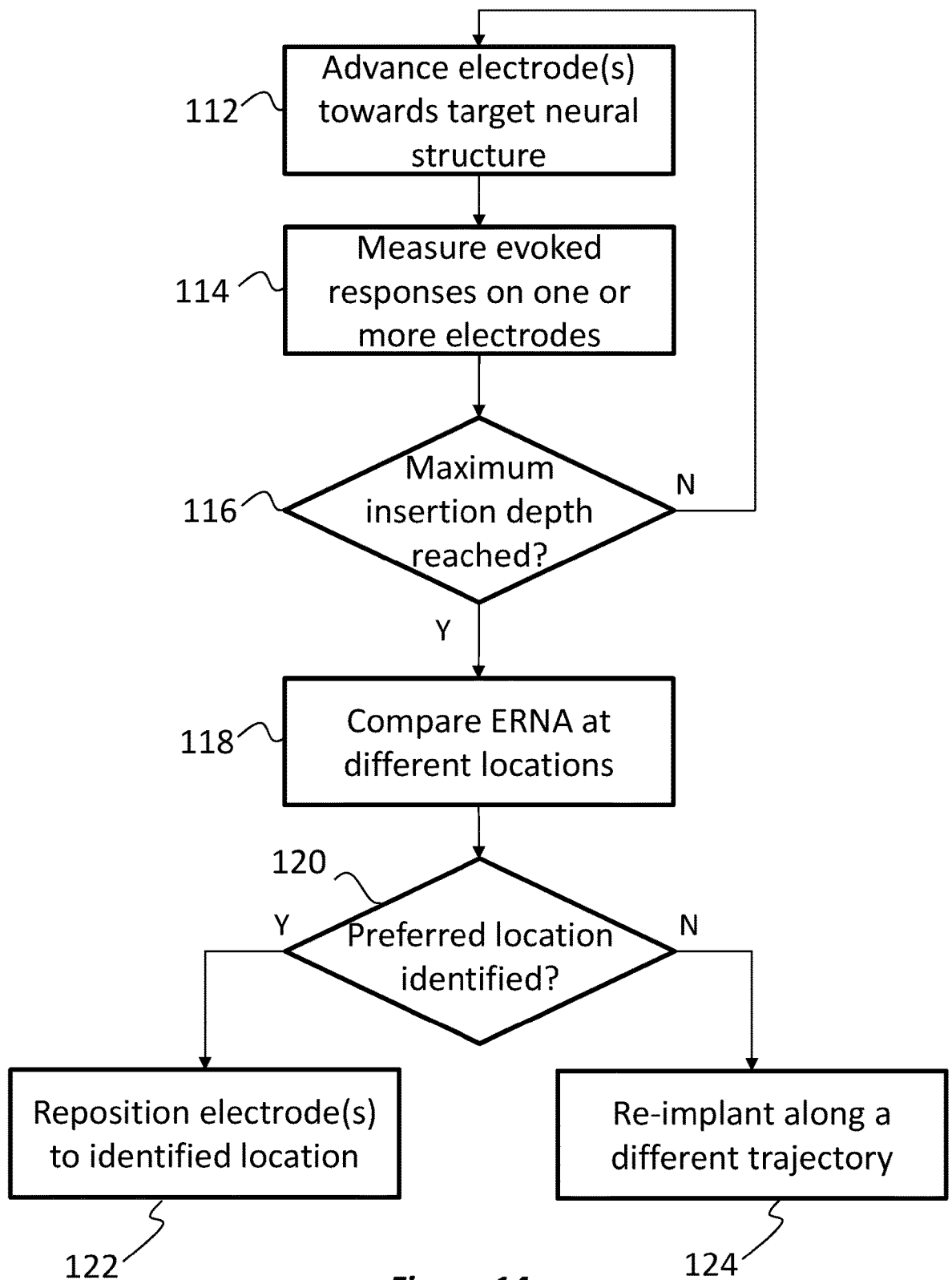
FIG. 14 is a flow diagram illustrating a process for locating a DBS electrode in the brain.

FIG. 14 shows a general example of such a process. The process begins at step 112 with an electrode lead tip such as that described with reference to FIG. 11 being advanced during surgery towards a target neural structure along a predefined trajectory. The step size (or spatial resolution) by which the electrode lead is advanced may be chosen by the surgeons and/or clinicians. In some embodiments, the step size is 1 mm. At step 114, evoked responses, including ERNA, are measured by applying a patterned stimulus such as those described above to an electrode of the lead tip 70. The stimulus may be applied for the whole time whilst the lead tip 70 is being implanted. Alternatively, the patterned signal may be repeated a predetermined number of times, such as 10 times. The evoked response may be measured at the same electrode as that used to apply the stimulus or may be measured at one or more different electrodes. By doing so, a more accurate estimate of the location of each electrode relative to the target neural structure may be provided. Steps 112 and 114 are repeated until the electrode lead tip has been inserted to the maximum allowable depth, which may be in the target neural structure or slightly beyond it.

By repeating steps 112 and 114, a profile or map of evoked responses at different locations along the insertion trajectory may be generated. The profile of evoked responses may include measurements from multiple electrodes or from just one electrode. The profile of evoked responses at different depths may be output to the one or more output devices 110. The profiles of evoked responses are then compared at step 118 in order to determine whether a preferred electrode location can be identified. The identification of preferred electrode location may be based on different ERNA features, including relative differences between or spatial derivatives of amplitude, rate of decay, rate of change, and frequency, at different insertion positions (e.g. the location that produces the largest resonances).

The identification of a preferred electrode location may also be based on comparison with template ERNA activity, where the templates have been derived from recordings from other patients. The profile of evoked responses may also be used to estimate the trajectory of the electrode lead 70 through the target neural structure, including the boundaries of the structure and the region intersected (e.g. the trajectory passed through the medial or lateral region). The profile of evoked responses may also be used to estimate the proximity to the target structure, in the event that the target structure is not intersected by the insertion trajectory.

If at step 120 a preferred electrode location can be identified, the electrode lead tip 70 can be repositioned at step 122, such that an electrode is positioned at the preferred location. Alternatively, for embodiments that include electrode lead tips with a large number of electrodes, the electrode positioned closest to the preferred location can be nominated for subsequent use in applying therapeutic stimulation. If at step 120 a preferred location cannot be identified, the surgeon and/or clinician may choose to remove the electrode and re-implant along a different trajectory.

Another embodiment of the present disclosure provides a system and method for determining the relative positions of an array of electrodes with respect to a target neural structure and then selecting a preferred electrode to use for applying therapeutic stimulation. This process could be performed during electrode implantation surgery to assist in the positioning of electrodes, or with previously implanted electrodes when programming the device to deliver therapeutic stimulation. A stimulus may be applied at more than one of the electrodes of the array, for example two or more of electrodes 72a, 72b, 72c, 72d in the case of electrode array 70. Where a patterned stimulation regime is used, sequential bursts of a stimulus pattern may be applied to different ones of the electrodes 72a, 72b, 72c, 72d. Alternatively, a full stimulus pattern may be applied at one electrode, followed by another full stimulus pattern at another electrode. By doing so, a determination may be made concerning which electrode of an electrode array is positioned best to provide therapeutic stimulation to one or more of the target neural structures; for example, which of the electrodes 72a, 72b, 72c, 72d is best positioned within a target neural structure.

Figure 15:
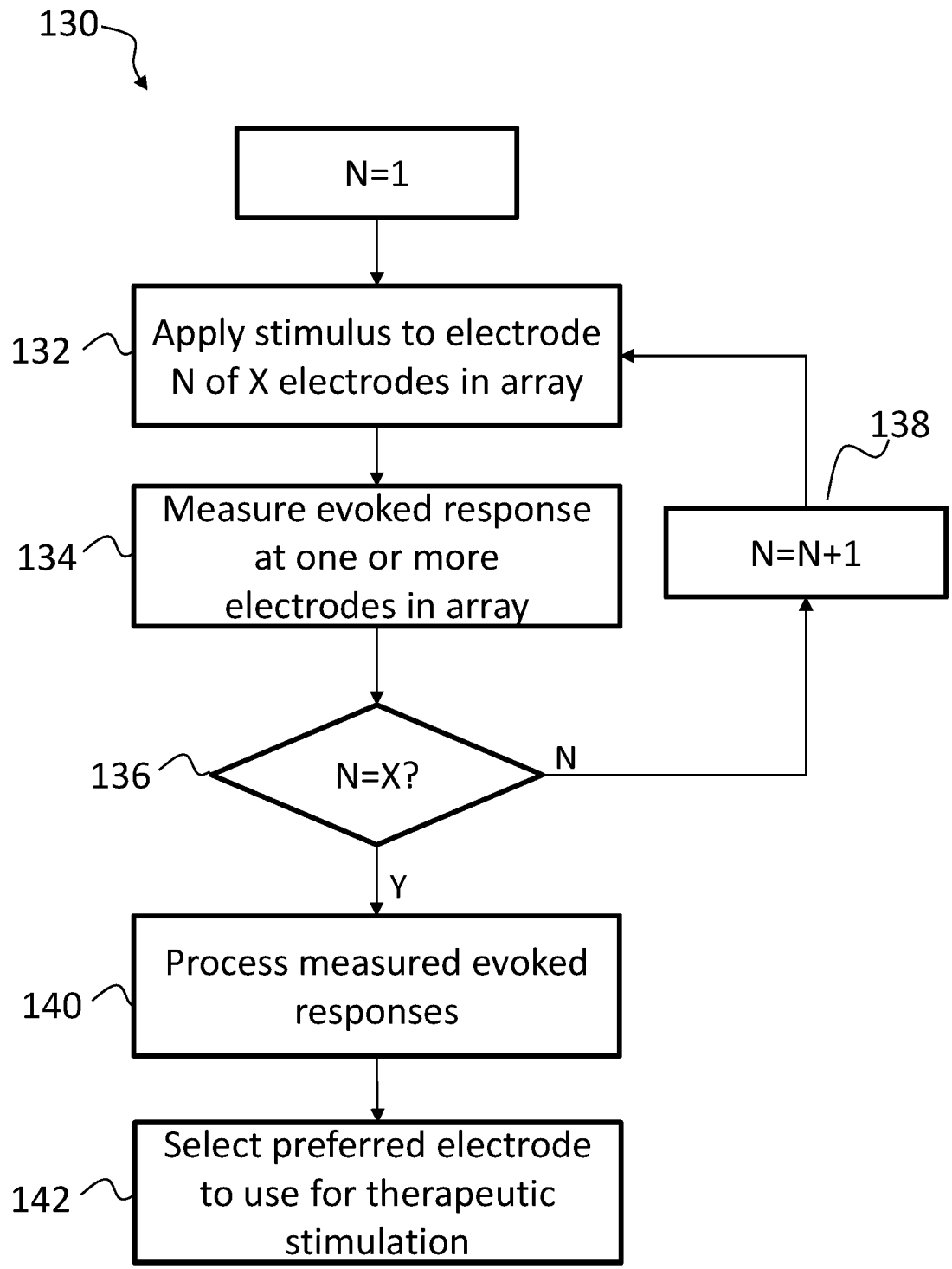
FIG. 15 is a flow diagram illustrating a process for monitoring and processing resonant responses at multiple electrodes in response to stimulation at multiple electrodes.

FIG. 15 illustrates an example process 130 for measuring evoked response from an array of multiple electrodes. At step 132, a stimulus is applied to the first electrode of an array of X electrodes (electrode 72a in the case of the lead tip 70). The stimulus applied may be a burst patterned stimulus as described above. The evoked response from a target neural structure is measured at one or more of the electrodes in the array at step 134. In the case of the lead tip 70, for example, the evoked response may be measured at the second, third and fourth electrodes 72b, 72c, 72d when the first electrode 72a is being stimulated. In some embodiments, the evoked responses received at the stimulating electrode may also be recorded and optionally stored in memory. Once the evoked response has been measured at each electrode, another electrode is selected for stimulation. This may be achieved by incrementing a counter, as shown in step 138, after the process has checked at step 136 to see whether all electrodes in the array of X electrodes have been stimulated, i.e. whether the process has cycled through all of the electrodes in the system. If there are electrodes remaining to be stimulated, then the process repeats, applying a stimulus to the next selected electrode in the array. If all electrodes in the array have been stimulated and an evoked response to stimulation at each electrode measured and recorded, the resultant measured evoked responses are then processed at step 140.

Processing the evoked responses may involve comparing different ERNA features, including relative differences between or spatial derivatives of amplitude, rate of decay, rate of change, and frequency, across different combinations of electrodes used for stimulation and measurement. For example, the processing may involve identifying the electrode that measures the largest evoked resonance amplitude for each stimulation condition). The identification of the preferred electrode location may also be based on a comparison with template ERNA activity. Templates may be derived from recordings from other patients or from one or more models or simulations.

Based on the processing of the evoked responses, a preferred electrode to use for therapeutic stimulation may be chosen at step 142. The results of the ERNA processing and a recommendation for the preferred electrode may be output to the one or more output devices 110. If the process has been performed during surgery, the results of the ERNA processing may also be used to determine which electrodes are within the target neural structure and whether to reposition the electrode array. The results may also be used to generate one or more templates for future processing of evoked responses in the same or different patients.

Figure 16:
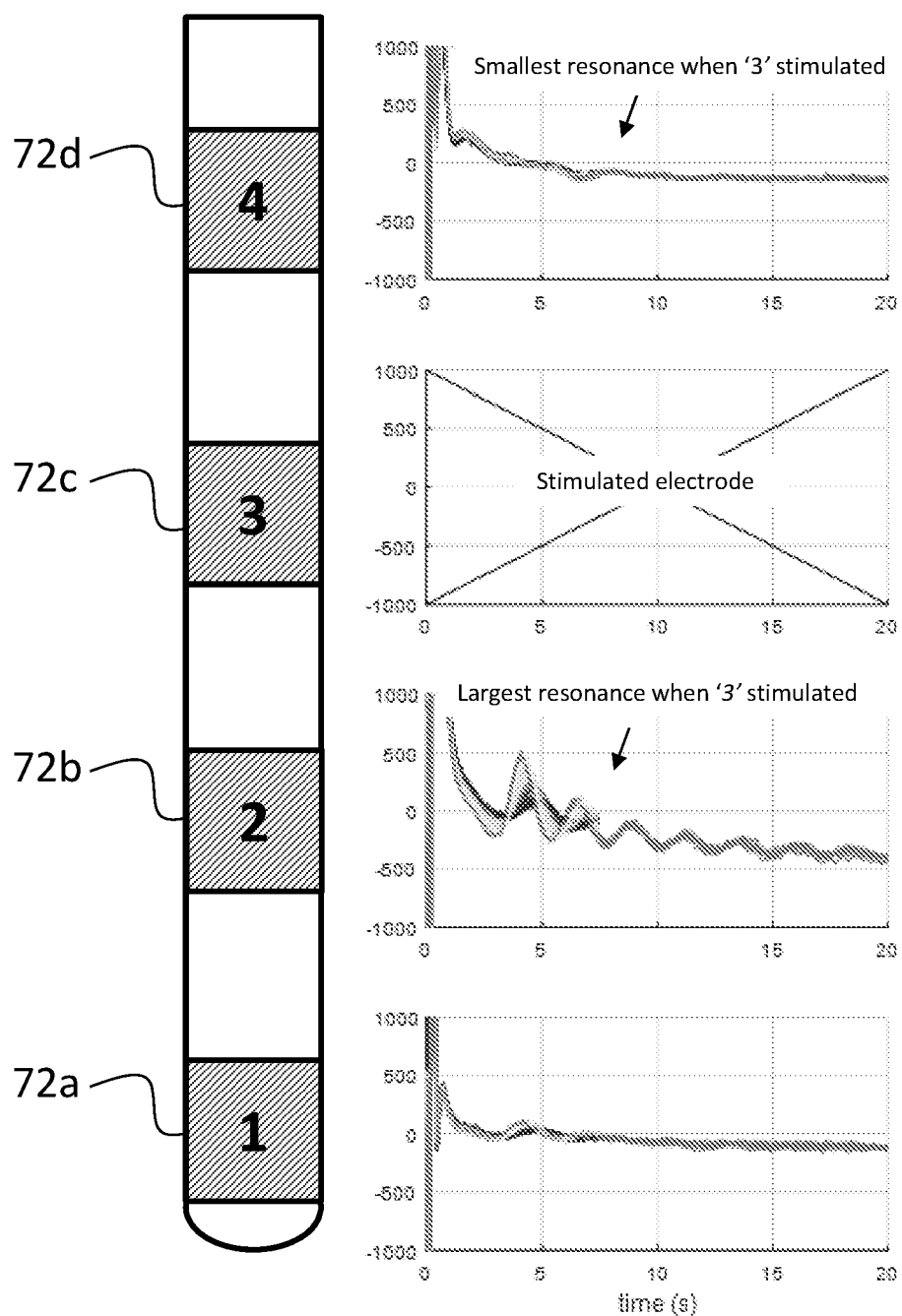
FIG. 16 is a graphical illustration of resonant responses measured at different electrodes implanted in a brain responsive to a stimulation signal in accordance with the process shown in FIG. 12.

FIG. 16 shows an example of the evoked responses measured at each of the first, second and fourth electrodes 72a, 72b, 72d based on patterned stimulation applied to the third electrode 72c. This example corresponds to one iteration of steps 132 and 134 of process 130 shown in FIG. 15. The stimulated electrode 72c is represented with the crossed axes. Firstly, it is shown that a resonant response over several cycles can be measured using the novel patterned stimulus. Secondly, it can be seen that the response at the second electrode 72b has the largest amplitude, the amplitude of response at the fourth electrode 72d has the smallest amplitude, and the amplitude of the evoked response at the first electrode 72a is substantially less than that at the second electrode 72b but slightly greater than that at the fourth electrode 72d. These results indicate that the second electrode 72b is closest to or within the target neural structure and the first and fourth electrodes 72a, 72d are outside of the target neural structure.

Whilst in the above example the evoked response is measured at three electrodes, in other embodiments, the evoked response may be measured at one or two or any number of electrodes in any configuration. For example, ERNA could be measured and/or recorded from different combinations of electrodes. Additionally or alternatively, measurement electrodes may be implanted in and/or positioned external to the brain or skull.

Figure 17:
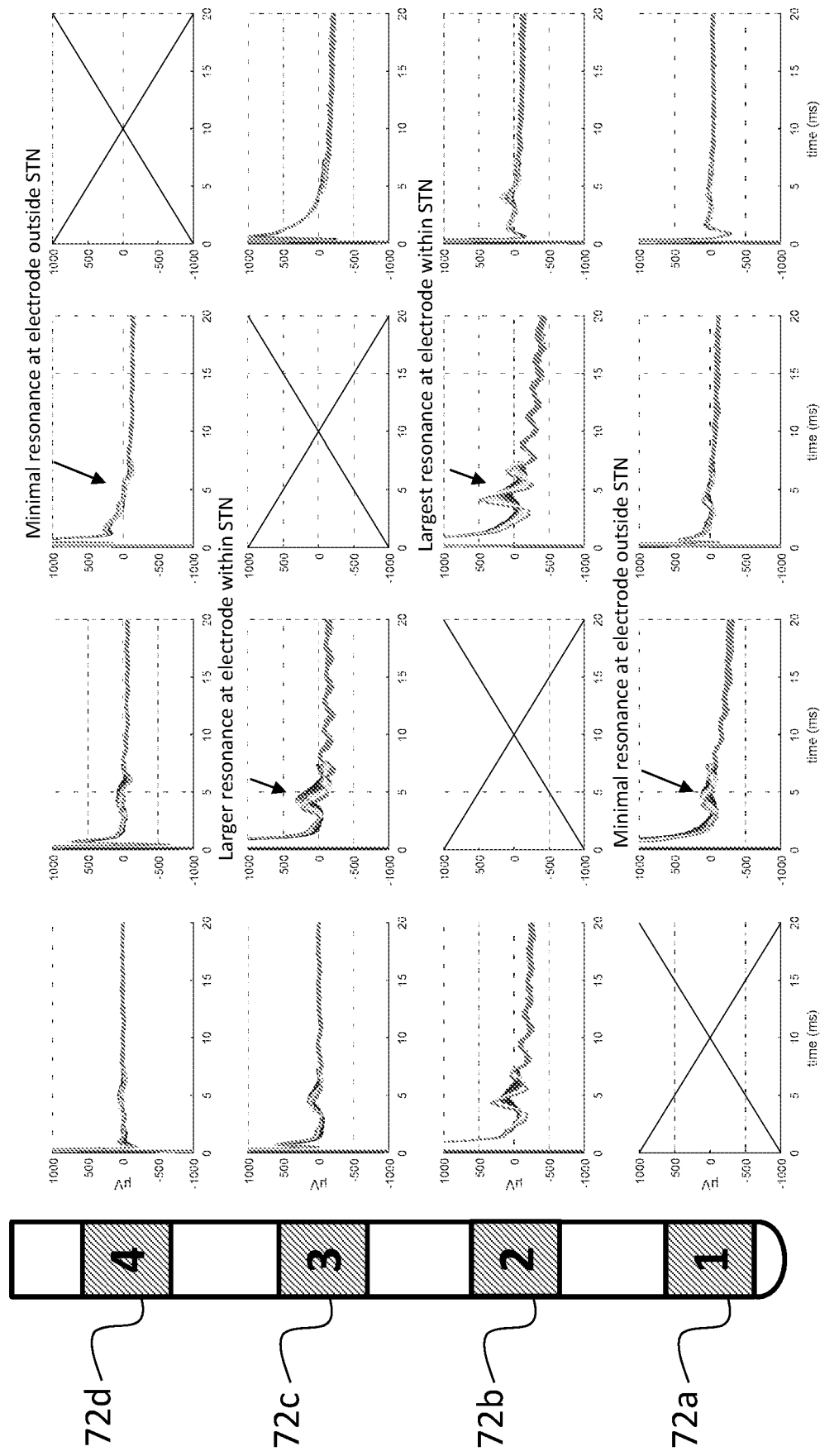
FIG. 17 is a graphical illustration of resonant responses measured at different electrodes implanted in a brain responsive to stimulation signals applied at different electrodes in accordance with the process shown in FIG. 12.

FIG. 17 graphically illustrates example evoked responses to stimulation in accordance with the process 130 of FIG. 15 applied to the lead tip 70 of the system 90 shown in FIG. 13. Each column of graphs represents one of four stimulation conditions with the stimulated electrode represented by the crossed panel, i.e. each column is an iteration of steps 132 and 134 of process 130. The data shown in FIG. 17 was measured with the second and third electrodes 72c, 72d positioned within the subthalamic nucleus (STN) of a patient's brain. It can be seen that the largest evoked responses are observed at each of the second and third electrodes 72b, 72c when the other of those electrodes 72c, 72b is stimulated. Accordingly, by comparing the measured evoked responses at each electrode in response to stimulation at another electrode, a determination can be made firstly of whether any of the electrodes are positioned within the target neural structure, secondly whether any of the electrodes are positioned at an optimum location within the target neural structure, and thirdly the direction and/or distance of a particular electrode from that target neural structure. In some embodiments, one or more of the presence, amplitude, natural frequency, damping, rate of change, envelope, and fine structure of an evoked resonant response to a stimulus may be used to identify the most effective electrode in an electrode array. Additionally, it can be seen that the evoked responses vary depending on the position of the electrode used for stimulation, illustrating the feasibility of using the process illustrated in FIG. 14 to localise electrodes within a target neural structure.

The process 130 of FIG. 15 may be repeated using different stimulation parameters (e.g. using different stimulation amplitudes or frequencies) or with more than one stimulating electrode in step 132 (e.g. stimulation applied concurrently through multiple electrodes on one or more electrode leads). The response characteristics obtained may be used to aid current steering (e.g. setting the distribution of currents across electrodes that are active simultaneously) and the selection of active electrodes (e.g. which electrodes to use for stimulation). For example, response characteristics can be used to estimate the spatial spread of activation relative to the target area. Using this information, the stimulation profile may be shaped using two or more electrodes to direct stimulation to particular areas of the brain, i.e. towards a target structure, and away from areas which the clinician does not wish to stimulate.

In a further embodiment, both ERNA and HFO activity can be used to optimize stimulation parameters used to target various medical conditions. For instance, once an electrode array such as the lead tip 70 has been accurately located within a target neural structure, the setting of stimulation parameters for therapeutic DBS can be aided by measuring ERNA and/or HFO activity, improving accuracy and time- and cost-efficiency, and reducing undesirable side-effects.

The change in elicited resonant activity and the measurement of HFO activity in local field potentials for different stimulation parameters may be used to optimize stimulation settings. Such processes can enable therapy to be tailored to the individual needs of patients and can be performed with minimal clinical intervention. In some embodiments, one or more of the presence, amplitude, natural frequency, damping, rate of change, envelope, and fine structure of an evoked resonant response to a stimulus may be used to optimise stimulation. Equally, in some embodiments, one or more of the presence, amplitude, frequency, damping, rate of change, envelope, and fine structure of an HFO measured in local field potentials during DBS stimulation may be used to optimise stimulation. Such response characteristics and HFO characteristics may be used to adjust amplitude, frequency, pulse width, and shape of a stimulation waveform.

A parameter of therapeutic stimulation that is particularly difficult to set using state of the art techniques is stimulation frequency. This is partly because optimum stimulation frequency can vary from patient to patient; typically between around 90 Hz to around 185 Hz. In embodiments of the present disclosure, one or more of the above described characteristics of ERNA and/or HFO activity may be used to set frequency of stimulation (e.g. the time period $t_2$ between pulses in a burst). For example, the stimulation frequency might be selected to approximate a multiple or submultiple of a frequency component of the ERNA, such as the estimated fundamental frequency of the ERNA. In another embodiment, the stimulation frequency can be selected to be dependent on a characteristic of the measured HFO activity, such as the HFO characteristic frequency. For example, the stimulation frequency may be selected to be half of a measured HFO characteristic frequency of a patient.

It will be appreciated that some or all of the parameters listed above may have synergistic or adverse effects on one another and thus the effectiveness of treatment. Accordingly, in some embodiments, known optimisation techniques such as machine learning or particle swarm may be implemented to find an optimal set of parameter values within the multidimensional parameter space. Such techniques may involve an iterative process of trying a selection of different parameter settings to determine the most effective parameter values based on the monitored ERNA and/or HFO activity.

To further optimise therapeutic DBS, the above techniques for ERNA and/or HFO activity monitoring and DBS parameter optimisation can be performed on a patient before and after administration of medication for relieving symptoms of a condition. For example, a record of ERNA for a particular patient who is on or off such medication may be used as a benchmark for an evoked resonant response which provides the most benefit to a patient so that parameters can be tuned to try to replicate such evoked response states. Equally, a record of HFO activity for a particular patient who is on or off such medication may be used as a benchmark for HFO activity which correlates with the most benefit to a patient so that parameters can be tuned to try to replicate such HFO activity.

Figure 18:
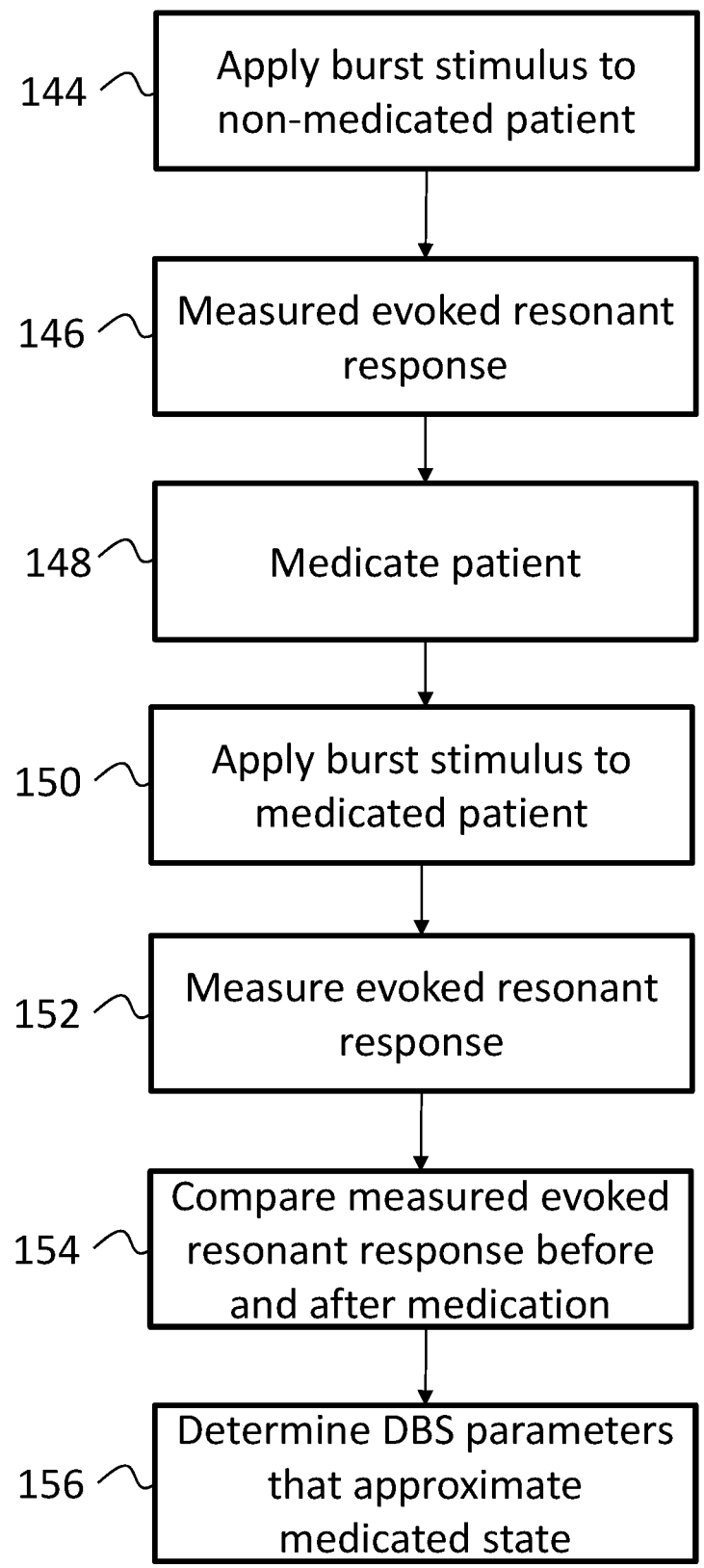
FIG. 18 is a flow diagram illustrating a process for determining parameters for a DBS stimulation signal based on medicating the patient.

FIG. 18 schematically illustrates a method of determining stimulation parameters based on the ERNA responsive to the stimulation of a medicated patient. At step 144, a stimulus is applied to an implanted electrode in a target neural structure of a patient before being administered with any medication, and the ERNA from the stimulus is measured and recorded at step 146. The patient is then medicated at step 148. For example, a clinician may administer a dose of a drug (e.g., levodopa) to the patient. At steps 150 and 152 the process of stimulation and measurement of resonant response are repeated. The ERNA before and after the medicament is administered is then used to determine stimulation parameters which approximate those of the patient's medicated state. In particular, DBS parameter settings may be chosen which, when administered, replicate or approximate the transition from the uncontrolled-symptom ERNA to the controlled-symptom ERNA.

Figure 19:
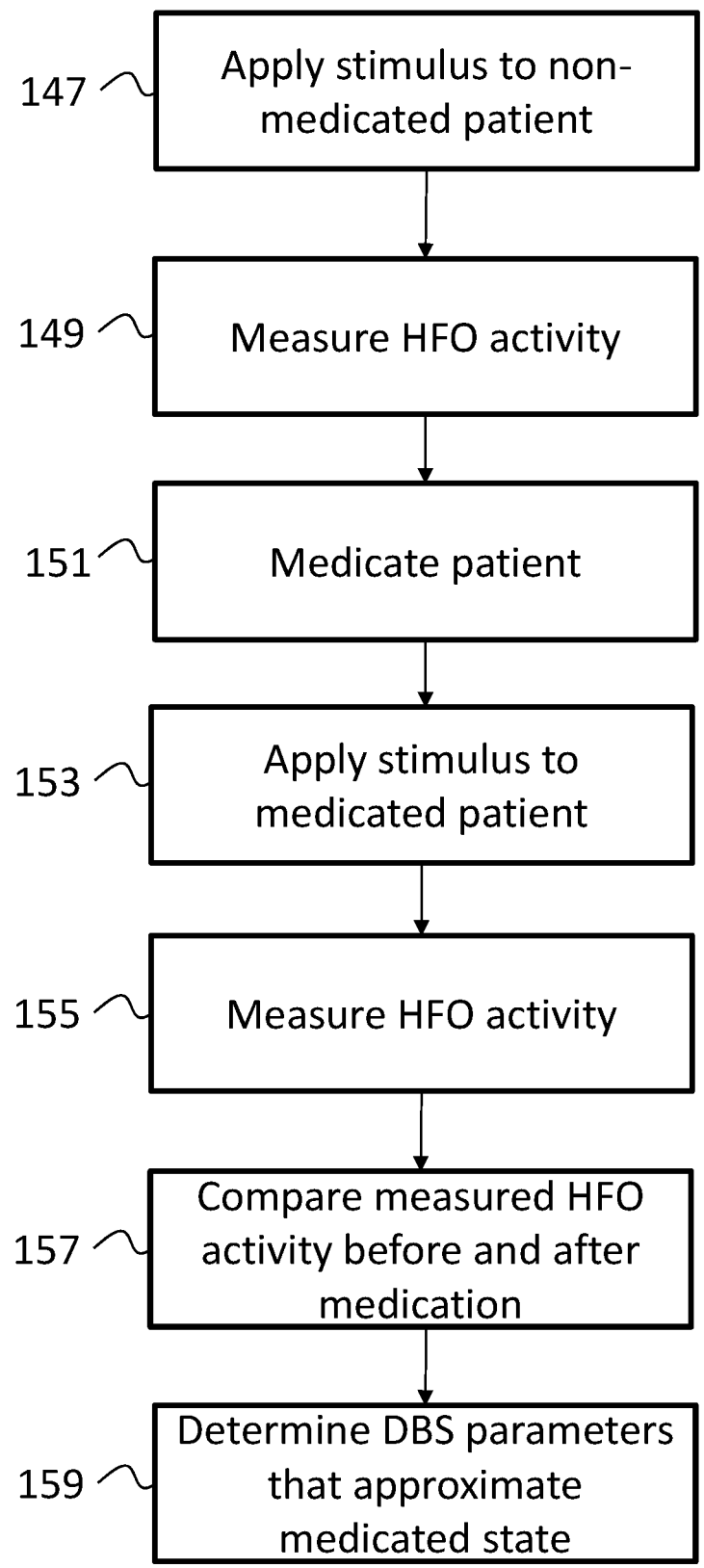
FIG. 19 is a flow diagram illustrating a process for determining parameters for a DBS stimulation signal based on medicating the patient.

FIG. 19 schematically illustrates a method of determining stimulation parameters based on the HFO activity responsive to the stimulation of a medicated patient. At step 147, a stimulus is applied to an implanted electrode in a target neural structure of a patient before being administered with any medication, and the HFO activity from the stimulus is measured and recorded at step 149. The patient is then medicated at step 151. For example, a clinician may administer a dose of a drug (e.g., levodopa) to the patient. At steps 153 and 155 the process of stimulation and measurement of resonant response are repeated. The HFO activity before and after the medicament is administered are then used to determine stimulation parameters which approximate those of the patient's medicated state. In particular, DBS parameter settings may be chosen which, when administered, replicate or approximate the transition from the uncontrolled-symptom HFO activity to the controlled-symptom HFO activity.

In some embodiments, optimisation processes may be performed by a clinician when the system 90 is being installed or during a visit to a healthcare centre. Additionally or alternatively, the optimisation may be run by the patient or may be instigated by the system 90 automatically. For example, the system 90 may implement an optimisation process periodically (e.g. every day, week or month). In other embodiments, an optimisation process could be initiated on replacement or recharge of a battery, in circumstances where the power source 106 includes a battery. Other conditions that could trigger an optimisation process include a change in the patient's state, such as whether the patient is engaged in a fine motor task, a gross motor task, speaking, sleeping, or is sedentary.

In some embodiments, the system 90 may store a series of previously optimised settings in the memory 102. These stored settings may correspond to the optimised settings for different patient states (e.g. fine or gross motor activation, sleeping or sedentary) and may include stimulation being applied to different target neural structures. The patient may be given the ability to choose which of the stored stimulation settings they want to use at any given time, through the use of a patient controller. Alternatively, the system 90 may automatically choose which of the stored stimulation settings to use based on measurements of the patients state from electrophysiological signals (e.g. ERNA or local field potentials (e.g. HFO activity)) recorded from the electrodes 70 by system 90 or from measurements taken with input devices 108 of the system 90 (e.g. accelerometers).

In addition to enhancing the accuracy of locating a DBS electrode in the brain, choosing electrode configurations for stimulation and optimising stimulation parameters, ERNA and HFO activity may be used to generate feedback for controlling the stimulation of electrodes. In some embodiments, feedback may be implemented using the system 90 shown in FIG. 13.

In one embodiment, the system 90 may use a waveform template corresponding to a preferred patient state. The template may be generated using previous recordings of ERNA and/or HFO activity in a patient with reduced symptoms. For example, ERNA/HFO templates recorded from a medicated patient or a patient receiving effective stimulation treatment may be used. Alternatively, ERNA/HFO templates recorded from a healthy patient, e.g. a patient without a movement disorder, may be used. Templates may be constructed from the average of many recordings from one patient or several patients. In some embodiments, selected features of the ERNA waveform and/or the HFO activity waveform may be used instead of a complete template. For example, parameters of the ERNA such as the dominant frequency and amplitude components and/or temporal features may be used to enable improved electrode placement and control of therapeutic stimulation. Equally, parameters of HFO such as characteristic frequency and amplitude components may be used to enable improved electrode placement and control of therapeutic stimulation. In some embodiments, preferred ranges for different ERNA characteristics may be defined (e.g. stimulation is controlled such that the ERNA frequency remains within 250-270 Hz). Equally, parameters of the HFO activity such as HFO characteristic frequency and amplitude components and/or temporal features may be used in the control of therapeutic stimulation. In some embodiments, preferred ranges for different HFO activity may be defined (e.g. stimulation is controlled such that the HFO frequency trends to 260 Hz, or such that rate of change of HFO frequency to characteristic frequency is greater than a predetermined threshold rate).

Figure 20:
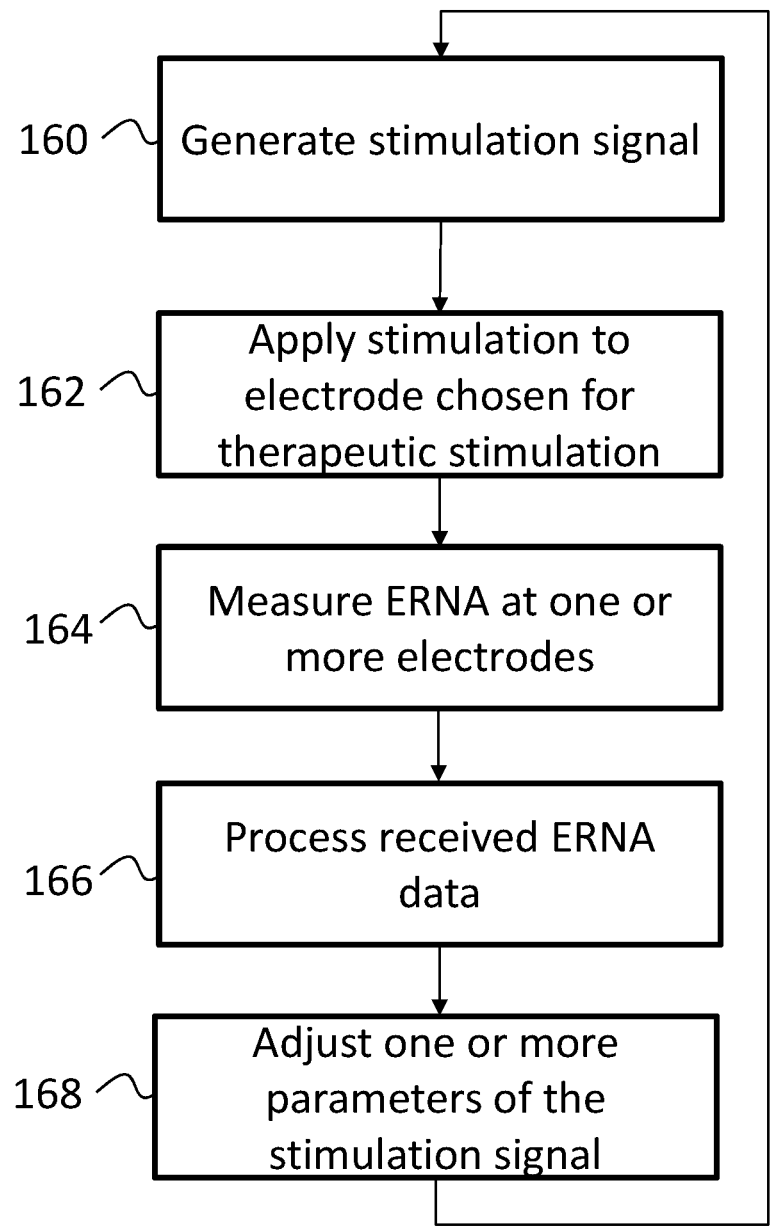
FIG. 20 is a flow diagram illustrating a process for generating a stimulation signal with closed-loop feedback based on evoked resonance at a target neural structure.

Referring to FIG. 13 and FIG. 20, in some embodiments, the processing unit 92 may send instructions/signals to the signal generator 94 to generate a stimulation signal, such as a patterned stimulation signal, which may or may not have been pre-calibrated in accordance with an embodiment described above. The signal generator 94 may then generate the signal at step 160 and apply it to one of the electrodes 72a, 72b, 72c, 72d of the lead tip 70 (step 162). The processing unit 92 may then measure the ERNA and monitor one or more parameters (or characteristics) of the ERNA (step 164). The processing unit 92 may then process the received ERNA data (step 166). In some embodiments, the processing unit 92 may compare the ERNA (or one more parameters thereof) with a resonant response associated with effective therapy (or one or more parameters thereof). Based on the ERNA data, the processing unit 92 may then instruct the signal generator to adjust one or more parameters of the stimulation signal applied to one of the electrodes 72a, 72b, 72c, 72d (step 168).

Figure 21:
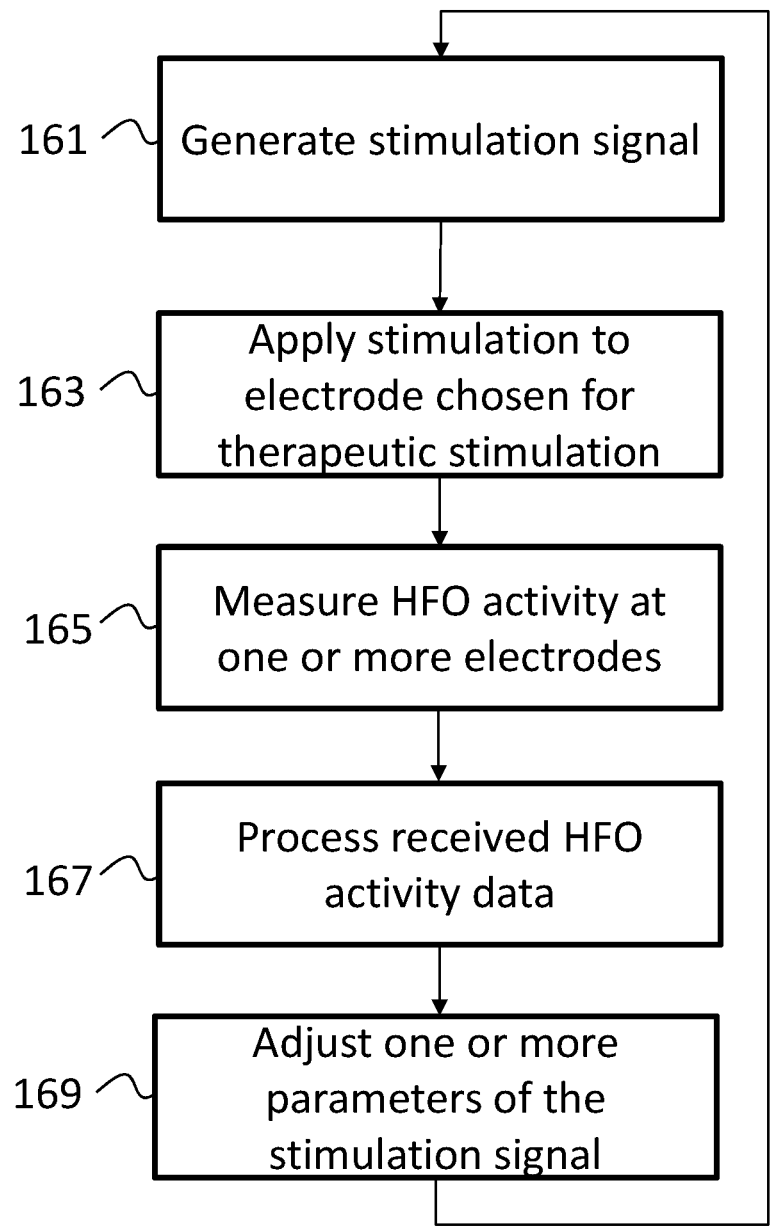
FIG. 21 is a flow diagram illustrating a process for generating a stimulation signal with closed-loop feedback based on HFOs from neuronal activity in the brain.

Referring to FIG. 13 and FIG. 21, in some embodiments, the processing unit 92 may send instructions/signals to the signal generator 94 to generate a stimulation signal, such as a patterned stimulation signal, which may or may not have been pre-calibrated in accordance with an embodiment described above. The signal generator 94 may then generate the signal at step 161 and apply it to one of the electrodes 72a, 72b, 72c, 72d of the lead tip 70 (step 163). The processing unit 92 may then measure the HFO activity and monitor one or more parameters (or characteristics) of the HFO activity (step 165). The processing unit 92 may then process the received HFO activity data (step 167). In some embodiments, the processing unit 92 may compare the HFO activity (or one or more parameters thereof) with HFO activity associated with effective therapy (or one or more parameters thereof). Based on the HFO activity data, the processing unit 92 may then instruct the signal generator to adjust one or more parameters of the stimulation signal applied to one or more of the electrodes 72a, 72b, 72c, 72d (step 169).

In some embodiments, the signal applied at step 161 may comprise multiple components each having a different frequency. For example, the signal may increase stepwise in frequency (e.g., 120 Hz, 130 Hz, 140 Hz, 150 Hz etc.). Alternatively or additionally, the multiple components of the signal applied at step 161 may each have a different amplitude. For example, the amplitude of the signal may increase stepwise in amplitude between components (e.g., 1 mA, 2 mA, 3 mA etc.).

The processing unit 92 may, at step 167, identity the HFO characteristic frequency of the HFO activity, i.e. the frequency to which the HFO activity is driven over time in the presence of the signal applied at step 161. In which case, at step 169, the signal may be adjusted so as to set the stimulation rate for therapy in dependence of the HFO characteristic frequency. For example, the stimulation rate may be chosen to be a sub-multiple of the HFO characteristic frequency (e.g., $f_{HFO}/1$, $f_{HFO}/2$, $f_{HFO}/3$ etc.), and preferably to a sub-multiple of half the HFO characteristic frequency.

Where the signal applied at step 161 comprises multiple components each having a different amplitude, the processing unit 92 may, at step 167, identify amplitudes of the applied signal at which HFO activity is promoted, driven to a particular frequency, and/or suppressed. At step 169, the amplitude of the signal may then be adjusted, for example, to the lowest that achieves the desired HFO activity effects. Desired effects may be compared with one or more templates as described above.

It will be appreciated that an iterative approach may be adopted in which optimum DBS frequency and amplitudes are determined based on HFO activity measured at one or more of the electrodes 72a, 72b, 72c, 72d.

In some embodiments, bursts of stimulation, such as those described above, in combination with the monitoring of ERNA and/or HFO activity may be used to identify a therapeutic resonant state (e.g. a state which correlates with good symptom suppression with minimal side effects and/or minimum electrical power consumption). From this information, therapeutic stimulation parameters required to produce the preferred therapeutic state may be identified. In some embodiments, these stimulation parameters may be used to apply continuous therapeutic DBS to the target neural structure.

Probe bursts for identifying resonant activity can be interleaved with the therapeutic DBS to re-assess the resonant state as well as HFO activity. These probe bursts may be implemented on a periodic basis, for example, every 10 seconds. In one embodiment, every 10 seconds, a probe burst may be applied for 1 second (e.g. 10 pulses at 130 Hz) and the ERNA and/or HFOs assessed. The therapeutic stimulation parameters may then be adjusted or maintained based on the ERNA and/or HFOs. For example, if there is a change in ERNA relative to the last probe burst, the stimulation parameters may be adjusted such that the ERNA becomes comparable with the previously measured ERNA and/or the template ERNA and/or an ERNA characteristic is within a desired range. Similarly, if there is a change in HFO activity relative to the last probe burst, the stimulation parameters may be adjusted such that the becomes comparable with the previously measured HFO activity and/or the template HFO and/or a HFO characteristic which is within a desired range.

There are a number of ways in which the therapeutic stimulation may be adjusted based on the measured ERNA. In some embodiments, if the resonant circuit is in a preferred resonant state, e.g. if the measured ERNA substantially matches a template or if an ERNA characteristic is within a desired range, the amplitude of the therapeutic stimulation may be reduced by the signal generator 94 in response to an instruction from the processing unit 92. Conversely, if the neural circuit is not in a preferred resonant state, the amplitude of therapeutic stimulation may be increased by the signal generator 94.

In some embodiments, if a therapeutic resonance is detected, the DBS stimulation may be switched off altogether or until after the next probe burst is applied to generate a measurable ERNA. Then when the next probe burst is applied, if the resonance is no longer therapeutic, the DBS stimulation may be switched back on.

In some embodiments, if a therapeutic resonance is detected, the DBS stimulation may be switched off altogether or until after the next probe burst is applied to generate a measurable ERNA. Then when the next probe burst is applied, if the resonance is no longer therapeutic, the DBS stimulation may be switched back on.

In some embodiments, the length of continuous stimulation blocks (between probe bursts) and the duration of the probe bursts may be adjusted to optimise the ERNA and/or HFO activity. Longer continuous stimulation periods or blocks between probe bursts will reduce the computation load on the processing unit 92 and thus increase power efficiency but may also result in greater variation of ERNA and/or HFOs from the preferred ERNA and/or HFOs and thus a reduction in effectiveness of treatment.

In previous paragraphs, the use of burst stimulation for identifying a therapeutic DBS state has been described in connection with ERNA. However, it has also been found that applying short bursts of stimulation (like those described above in relation to ERNA) appears to promote HFO activity without shifting the frequency of that activity. Such bursts can, therefore, be used to elevate HFO power to measurable levels, allowing them to be evaluated without the need for simultaneous therapeutic DBS. Accordingly, bursts of stimulation can also be used in combination with the monitoring of HFO activity in several ways. For example, enhanced HFO activity can be used in the identification of a therapeutic DBS state (e.g. a state which correlates with good symptom suppression with minimal side effects and/or minimum electrical power consumption). Additionally, therapeutic stimulation parameters required to produce the preferred therapeutic state may be identified. In some embodiments, these stimulation parameters may be used to apply continuous therapeutic DBS to the target neural structure.

As with the use of ERNA, there are a number of ways in which the therapeutic stimulation may be adjusted based on measured HFOs. In some embodiments, if the measured HFO activity is in a preferred state, e.g. if the measured HFOs substantially match a template or if an HFO characteristic frequency is within a desired range, the amplitude of the therapeutic stimulation may be reduced by the signal generator 94 in response to an instruction from the processing unit 92. Conversely, if the HFOs are outside of the preferred state, the amplitude of therapeutic stimulation may be increased or decreased by the signal generator 94 to reposition the HFO activity within the preferred window.

In addition to the above, since the application of non-therapeutic patterned stimulation also enhances HFO activity, such activity can be used to track the effects of medication, a disease state or to assist in the placement of electrodes or to decide which electrode of a plurality of electrodes positioned within the brain is the optimal electrode to use for stimulation. To that end, equivalent methods to those described herein both for electrode placement and choosing which electrode to use for DBS based on ERNA, can also be used to aid in the placement of electrodes and choose an optimal electrode for stimulation.

Figure 22:
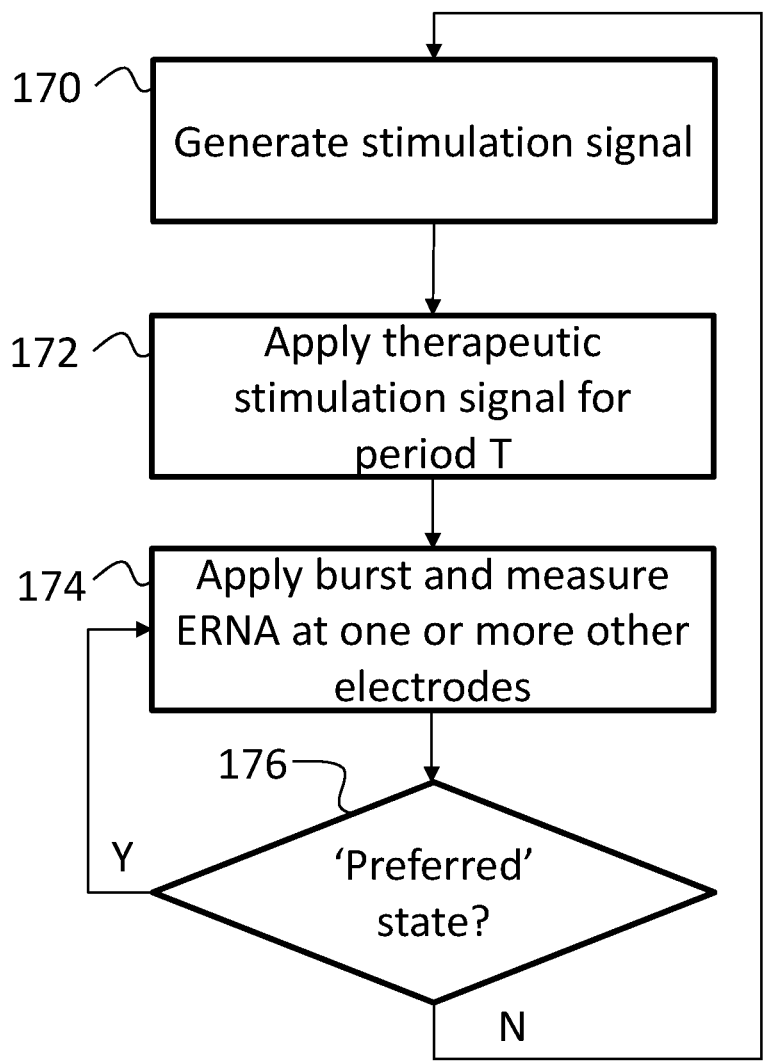
FIG. 22 is a flow diagram illustrating another process for generating a stimulation signal with closed-loop feedback based on evoked resonance at a target neural structure.

There is an inherent requirement for implanted and portable DBS devices to provide the best treatment of symptoms while minimising both side effects and power consumption. In one embodiment, a method for operating the system 90 using closed-loop feedback is provided in which the duty cycle of stimulation is modulated with an aim to minimise stimulation on-time. FIG. 22 illustrates a process which may be performed by the system 90. At step 170 a stimulation signal is generated. Parameters of the stimulation signal are chosen so as to optimise the ERNA and/or HFO activity to preferred states. The stimulus is then applied to an electrode of the lead tip 70 for a period T at step 172. The period T may be a fixed period. Preferably the stimulus is applied continuously or periodically until a preferred state of ERNA is reached. The therapeutic stimulation is then stopped and the evoked response are measured at one or more electrodes, the evoked response being to a probe stimulus comprising one or more bursts of pulses applied to the stimulation electrode (at step 174). In some embodiments the probe stimulus may be applied to more than one electrode. In some embodiments, the stimulation electrode can be used to measure ERNA instead of or in addition to the one or more other electrodes. The system is then maintained in this state of monitoring until the ERNA becomes undesirable. In some embodiments, the determination of whether or not the ERNA is in a preferred or therapeutic state may be performed by comparing the measured response with a template ERNA response, or by comparing a measured ERNA characteristic with a desired range. As soon as it is considered that the state is undesirable at step 176, a stimulation signal is again generated and applied at steps 170 and 172.

Figure 23:
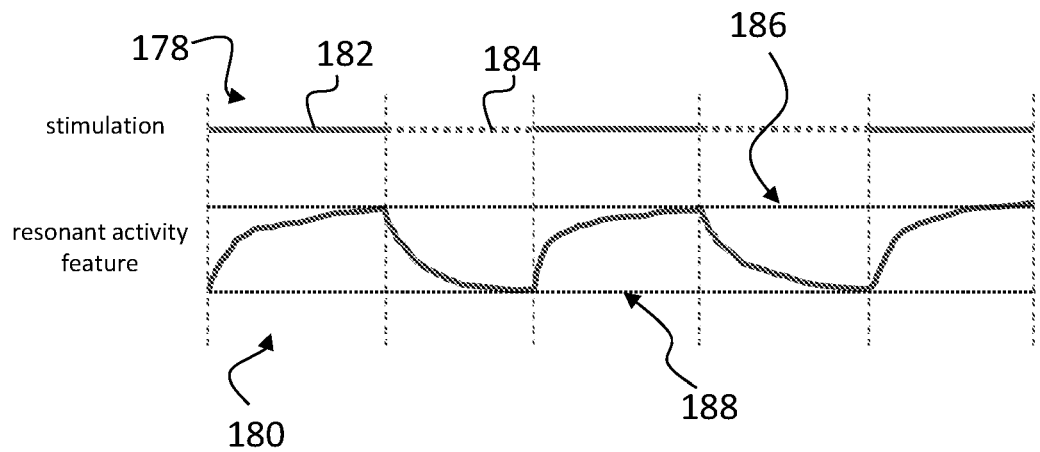
FIG. 23 graphically illustrates switching between periods of therapeutic and non-therapeutic stimulation relative to a resonant activity feature of an evoked response in accordance with the process of FIG. 17.

FIG. 23 graphically compares a stimulation regime 178 comprising a patterned therapeutic stimulation signal 182 followed by a non-therapeutic patterned stimulation signal (comprising one or more bursts of pulses) 184 and a corresponding characteristic (e.g. resonant frequency) 180 of the ERNA varying between a preferred state 186 and a less than preferable state 188.

Figure 24:
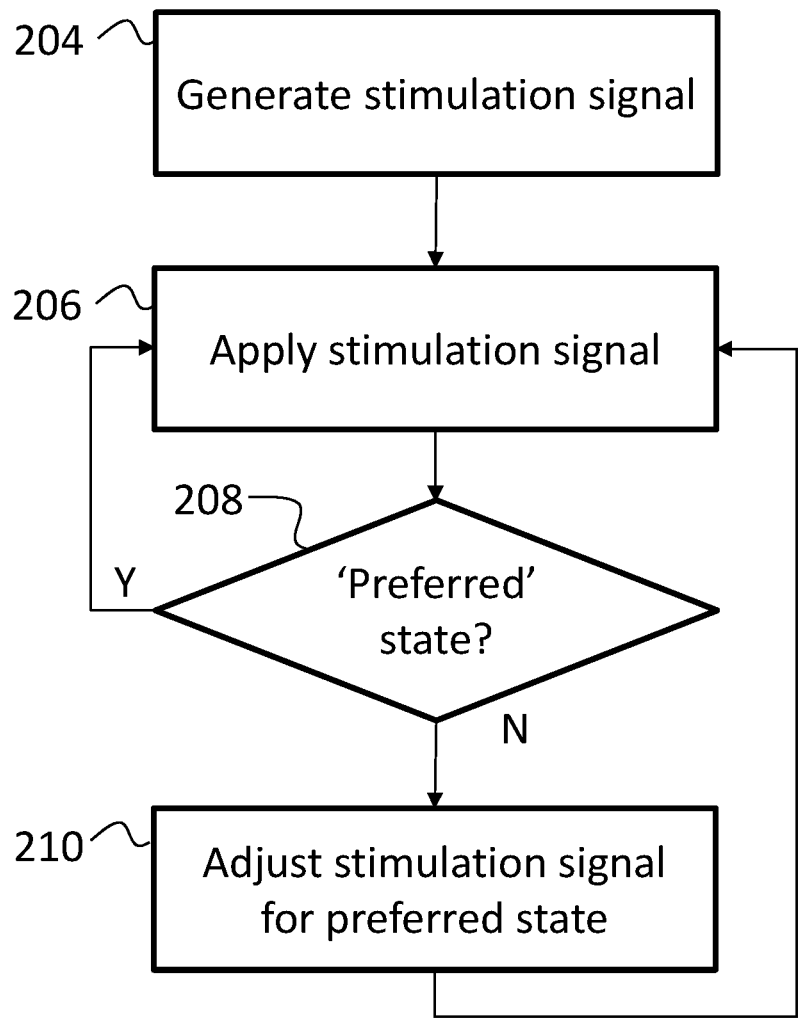
FIG. 24a illustrates a patterned stimulation signal according to an embodiment of the present disclosure.
FIG. 24b illustrates another patterned stimulation signal according to an embodiment of the present disclosure.

A method for operating the system 90 using closed loop feedback has been described above in relation to ERNA. However, in one embodiment, a method for operating the system 90 using closed-loop feedback is provided in which HFO activity is used to control DBS stimulation in realtime. FIG. 24 illustrates a process which may be performed by the system 90. At step 204 a stimulation signal is generated. Parameters of the stimulation signal are chosen so as to optimise the HFO activity to a preferred state. The stimulus is then applied to an electrode of the lead tip 70 at step 206. Preferably the stimulus is applied continuously or periodically until a preferred state of HFO is reached. Whilst the stimulation signal is begin applied to the lead tip 70, HFO activity is measured at one or more electrodes (at step 174). In some embodiments the stimulation signal may be applied to more than one electrode. In some embodiments, the stimulation electrode can be used to measure HFO activity instead of or in addition to the one or more other electrodes. In some embodiments, the system 90 continues to monitor HFO activity until the HFO activity becomes undesirable. In some embodiments, the determination of whether or not the HFO activity is in a preferred or therapeutic state may be performed by comparing the measured activity with a template HFO activity or by comparing a measured HFO characteristic with a desired range. As soon as it is considered that the state is undesirable at step 210, the stimulation signal is adjusted and applied at step 206 to the lead tip 70.

Figure 25:
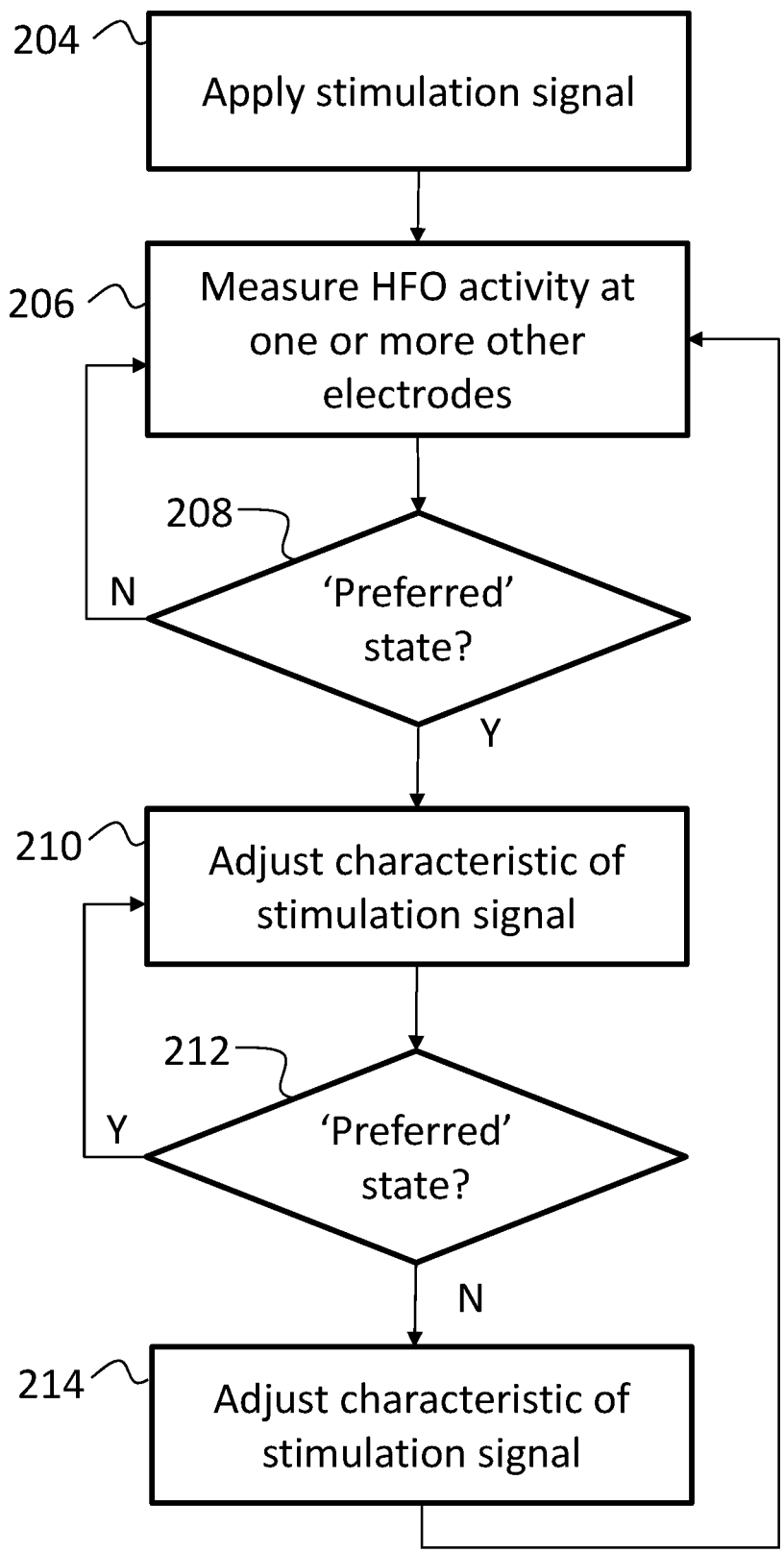
FIG. 25 is a flow diagram illustrating another process for generating a stimulation signal with closed-loop feedback based on HFOs from neuronal activity in the brain.

FIG. 25 illustrates another process which may be performed by the system 90 for controlling DBS stimulation. At step 204 a stimulation signal is generated. Parameters of the stimulation signal are chosen so as to optimise the HFO activity to a preferred state. The stimulus is then applied to an electrode of the lead tip 70 at step 206. Preferably the stimulus is applied continuously or periodically until a preferred state of HFO is reached. Whilst the stimulation signal is begin applied to the lead tip 70, HFO activity is measured at one or more electrodes (at step 206). In some embodiments the stimulation signal may be applied to more than one electrode. In some embodiments, the stimulation electrode can be used to measure HFO activity instead of or in addition to the one or more other electrodes. Stimulation is applied until HFO activity reaches an optimum state. In some embodiments, the determination of whether or not the HFO activity is in an optimum state may be performed by comparing the measured activity with a template HFO activity or by comparing a measured HFO characteristic with a desired range. When, at step 208, HFO activity is measured as being in an optimum state, at step 210, the applied DBS stimulation amplitude or frequency may be adjusted, for example, by reducing its amplitude of frequency or by ceasing stimulation altogether. This in turn will cause the HFO activity to drift outside of the preferred state. When, at step 212, the HFO activity is found to no longer be in a preferred state, the HFO activity may then be adjusted again at step 214 to bring the HFO activity back to the preferred state, for example, by increasing the amplitude of DBS stimulation or by adjusting the frequency of stimulation.

Figure 26A:
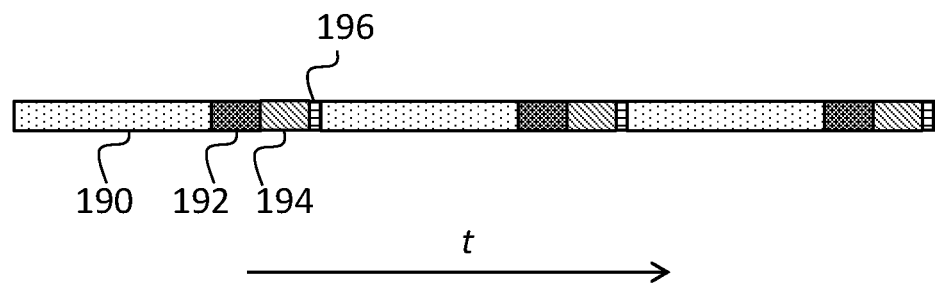
FIG. 26 graphically illustrates Washout in the 200-400 Hz washout over consecutive 15 s periods post-DBS and in the last 15 s pre-DBS for 19 brain hemispheres.
Figure 26B:
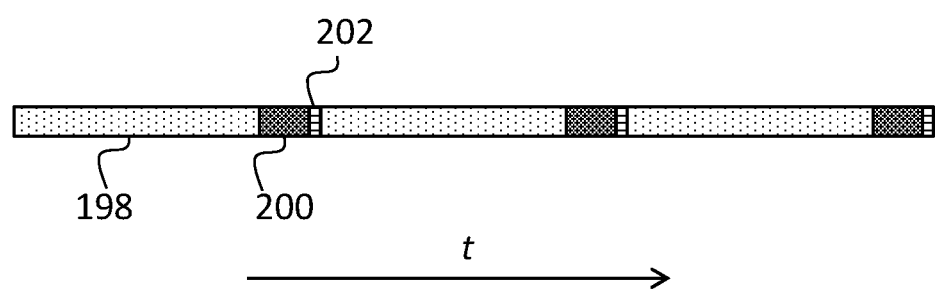

There are several different ways of implementing the patterned signals of embodiments described herein. FIGS. 26a and 26b illustrate two exemplary patterning profiles. In FIG. 26a, the patterned profile includes a period of no stimulation 192 after a continuous stimulation block 190, followed by a burst of pulses 194 and another period of no stimulation 196. During the period of no stimulation, the ERNA may be measured and therapeutic stimulation signal adjusted (if required). HFO activity may be measured either during the period of no stimulation, or during stimulation, or both, and therapeutic stimulation may be adjusted accordingly, if required.

In an alternative embodiment, the system may monitor the ERNA and/or HFO activity after a final pulse of continuous stimulation 198 as shown in FIG. 26b. After a period of monitoring 200, the therapeutic stimulation may then be adjusted for a period 202 after which the therapeutic stimulation 198 may be applied with the adjusted parameters. This regime may also be considered as continuous stimulation with periodic missing pulses. To this end, the continuous stimulation may be considered as a burst of pulses, and the period of no stimulation may be considered as the first time period $t_1$ as described with reference to FIG. 2 above.

The presence and amplitude of ERNA and HFO activity can be dependent on stimulation amplitude. Accordingly, so as to maintain consistency in measurements of both ERNA and HFO, it may be preferable to always use the same pulse parameter settings. In particular, it may be preferable to use the same amplitude for the pulse used for pulse parameter settings and for the pulse used to measure ERNA. The last pulse before the period of no stimulation may therefore be at a fixed amplitude which is independent of the amplitude of stimulation being applied by other pulses (e.g. therapeutic stimulation), so as to minimise any effect due to resonance dependence on stimulation amplitude or other pulse parameters.

Whilst in embodiments described above, a single electrode array is used both to stimulate and record an evoked neural response, in other embodiments, electrodes may be distributed on multiple probes or leads in one or more target structures in either or both brain hemispheres. Equally, electrodes either implanted or positioned external to the brain may be used to stimulate or record or both stimulate and record an evoked neural response. In some embodiments, a combination of both microelectrode and macroelectrodes may be used in any foreseeable manner.

In a further application of the embodiments of the present invention ERNA and/or HFO measurements may be recorded and tracked over time to monitor the progression or remission of a disease or syndrome, or used as a diagnostic tool (e.g. to classify the patient's neurological condition). Such embodiments may also be used to provide medical alerts to the patient, a caregiver or a clinician in the event that the patient's state (as determined by ERNA/HFO activity) deteriorates towards an undesirable or critical state (e.g. a Parkinsonian crisis).

In yet another application, ERNA and/or HFO activity may be used to monitor the effects of medication over time, including the effects of adjusting medication doses, etc.

Such an embodiment may also be used to provide medication alerts to the patient to remind them when a dose is required or when a dose has been skipped. Tracking medication effects with ERNA/HFO activity may also provide clinicians with information regarding whether medication is being taken as prescribed or whether medication is becoming less effective and requires dosing adjustment.

Further Analysis of HFO Activity and Explanation of Results

The neural activity resulting from DBS pulses was investigated to determine if HFOs could be used as a biomarker. A wide recording bandwidth was used, as well as symmetric biphasic pulses for stimulation, rather than conventional asymmetric pulses with a very long second phase, to minimize the temporal duration of stimulation artefacts.

Recordings were made from DBS electrodes immediately following their implantation in the STN of patients with Parkinson's Disease (PD) who were still awake on the operating table, as PD is the predominant application for DBS. Furthermore, the STN's roles in regulation of motor, limbic, and associative function make it a neural target relevant to a number of different applications, including DBS treatment of dystonia, essential tremor, epilepsy, and obsessive-compulsive disorder.

Standard 130 Hz DBS was temporally patterned to allow multiple peaks to be observed. We employed two novel patterns: skipping one pulse every second, and applying a burst of ten pulses every second. The 'skipped-pulse' pattern was anticipated to have comparable therapeutic effects to standard 130 Hz DBS, as it causes only a 0.77% reduction in the total number of pulses delivered over time. In contrast, the 'burst' pattern was anticipated to have minimal therapeutic effects relative to continuous DBS, as only 7.7% of the pulses are delivered, making it a useful probe for investigating activity in the absence of therapy.

We applied the burst stimulus to the STN of 12 PD patients (n=23 hemispheres) undergoing DBS implantation surgery and observed HFOs of similar morphology in all cases, indicating it is a robust and reliable signal that can be measured across the patient population.

Figure 26:
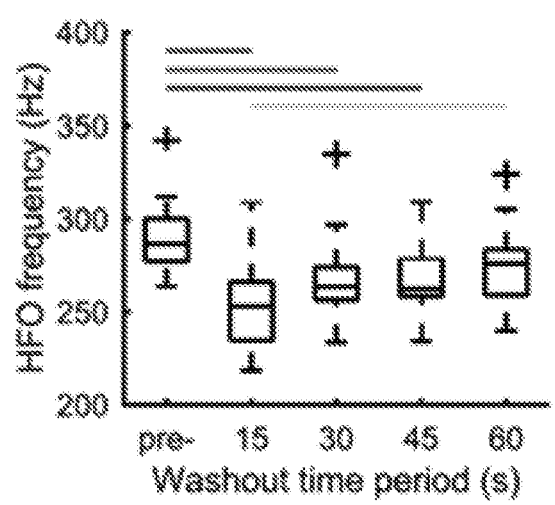

As the HFO activity was generally characterized by a broadband peak in frequency, we calculated multitaper spectral estimates and then determined the frequency and amplitude of the peak occurring between 200-400 Hz. Comparing averages across 15 s non-overlapping blocks (FIG. 26), we found HFO peak frequency to be significantly decreased post-DBS (Friedman, $\chi^2(4)$=45.18, p<0.001), until the final 45-60 s block (Tukey, p=0.077). This washout trend matches that for ERNA frequency, albeit at a lower frequency, with a significant correlation between the two (Pearson product moment, $\rho$=0.546, n=152, p<0.001). The median HFO peak frequency immediately post-DBS was 253 Hz, comparable to the median ERNA frequency of the therapeutic 3.38 mA condition (256 Hz), suggesting HFO activity occurs at the same frequency as ERNA during the more continuous skipped-pulse stimulation.

No significant differences were found in HFO peak amplitude (Friedman, $\chi^2(4)$=2.11, p=0.72), although it did significantly correlate with ERNA amplitude (Pearson product moment, $\rho$=0.429, n=152). It is likely that the very small amplitude (<1 µV) of HFO peaks resulted in any modulatory effects being obscured by noise in the recordings.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A method for monitoring neural activity responsive to a stimulus in a brain, the method comprising:
    a. applying a first stimulus to one or more of at least one electrode implanted in the brain, the first stimulus comprising a first plurality of bursts of stimulation,
    b. detecting high frequency oscillations (HFOs) between about 200 Hz and about 500 Hz due to neuronal activity at one or more of the at least one electrode implanted in the brain at least partially during application of the first stimulus;
    c. determining one or more waveform characteristics of the HFOs; and
    d. generating a second stimulus comprising a second plurality of bursts of stimulation, wherein one or more waveform characteristics of the second stimulus is dependent on the one of more waveform characteristics of the HFOs; and
    e. applying the second stimulus to one or more of the at least one electrode implanted in the brain.

2. The method of claim 1, wherein the first plurality of bursts comprises a first burst applied for a first time period and having a first waveform characteristic and at least a second burst applied for a second time period following the first time period and having a second waveform characteristic.

3. The method of claim 2, wherein detecting HFOs due to neuronal activity at one or more of the at least one electrode implanted in the brain further comprises:
    detecting a first high frequency oscillation (HFO) during the first time period and at least a second HFO during the second time period at one or more of the at least one electrode implanted in the brain.

4. The method of claim 1, wherein the one or more waveform characteristics of the HFOs comprises one or more of the following:
    a) a frequency;
    b) an amplitude;
    c) a rate of change of frequency;
    d) a rate of change of amplitude; and
    e) a bandwidth.

5. The method of claim 1, wherein the first plurality of bursts and/or the second plurality of bursts are separated by a first pattern time period, each burst comprising a plurality of pulses separated by a second pattern time period, wherein the first pattern time period is greater than the second pattern time period.

6. The method of claim 5, wherein two or more of pulses within at least one of the first plurality of bursts have different amplitudes and/or wherein two or more of pulses within at least one of the second plurality of bursts have different amplitudes.

7. The method of claim 5, wherein the amplitude of a final pulse in each of the first plurality of bursts is substantially identical or wherein the amplitude of a final pulse in each of the second plurality of bursts is substantially identical.

8. The method of claim 1, wherein the one or more waveform characteristics of the second stimulus comprises a frequency, and wherein the frequency is configured to be equal to the frequency of the HFO divided by 1, 2, 3 or 4.

9. The method of claim 1, wherein the one or more waveform characteristics of the HFOs comprises a rate of change of frequency and wherein the one or more characteristics of the second stimulus are configured to maximise the rate of change of the frequency of the HFOs.

10. The method of claim 1, further comprising:
determining a correlation between the detected HFOs and a HFO template; and wherein the second stimulus is generated based on the correlation.

11. The method of claim 1, further comprising:
whilst applying the second stimulus, simultaneously detecting high frequency oscillations (HFOs) due to neuronal activity at one or more of the at least one electrode implanted in the brain; and
determining one or more second waveform characteristics of the detected HFOs during application of the second stimulus.

12. The method of claim 11, further comprising:
estimating a degree of progression of a disease associated with the patient based on the one or more first waveform characteristics of the HFOs and the one or more second waveform characteristics of the HFOs; or
determining the effect of a therapy provided to the patient based on the one or more first waveform characteristics of the HFOs and the one or more second waveform characteristics of the HFOs.

13. The method of claim 11, further comprising:
comparing a common waveform characteristic between the one or more waveform characteristics and the one or more second waveform characteristics.

14. The method of claim 13, wherein the steps of applying the second stimulus whilst simultaneously determining one or more second waveform characteristics of the HFOs are repeated until it is determined that one or more of the at least one electrode is positioned in a target neural structure in the brain.

15. The method of claim 11, further comprising:
selecting one or more of the at least one electrode to use for therapeutic stimulation of a target neural structure in the brain based on the one or more waveform characteristics or the one or more second waveform characteristics; and
applying a therapeutic stimulus to the target neural structure via the selected one or more of the at least one electrode.

16. The method of claim 11, further comprising:
inserting the at least one electrode into the brain along a predefined trajectory;
wherein the steps of applying the second stimulus whilst simultaneously determining one or more second waveform characteristics of the HFOs are repeated while the at least one electrode is being inserted to generate a profile of HFO activity with respect to the predefined trajectory and a target neural structure in the brain.

17. The method of claim 1, further comprising:
e. detecting a resonant response from the target neural structure evoked by the stimulus at one or more of the at least one electrode in or near a target neural structure of the brain; and f. determining one or more waveform characteristics of the detected resonant response.

18. The method of claim 1, wherein the HFOs have a frequency of between about 230 Hz and about 330 Hz.

19. A neuromodulation system, comprising:
a lead having at least one electrode adapted for implantation in or near a target neural structure in the brain;
a signal generator selectively coupled to one or more of the at least one electrode and configured to:
generate and apply a first stimulus to one or more of the at least one electrode, the first stimulus comprising a first plurality of bursts of stimulation; and
generate and apply a second stimulus to one or more of the at least one electrode, the second stimulus comprising a second plurality of bursts of stimulation;
a measurement device selectively coupled to one or more of the at least one electrode and configured to detect high frequency oscillations (HFOs) between about 200 Hz and about 500 Hz generated from neural activity at one or more of the at least one electrode when implanted in the brain at least partially during application of the first stimulus; and
a processing unit coupled to the measurement device and configured to determine one or more waveform characteristics of the detected HFOs,
wherein one or more waveform characteristics of the second stimulus is dependent on the one of more waveform characteristics of the HFOs.

20. A method for monitoring neural activity responsive to a stimulus in a brain, the method comprising:
a. applying a first stimulus to one or more of at least one electrode implanted in the brain, the first stimulus comprising a first plurality of bursts of stimulation,
b. detecting high frequency oscillations (HFOs) due to neuronal activity at one or more of the at least one electrode implanted in the brain at least partially during application of the first stimulus;
c. determining one or more waveform characteristics of the HFOs; and
d. generating a second stimulus comprising a second plurality of bursts of stimulation, wherein one or more waveform characteristics of the second stimulus is dependent on the one of more waveform characteristics of the HFOs; and
e. applying the second stimulus to one or more of the at least one electrode implanted in the brain,
wherein the first plurality of bursts and/or the second plurality of bursts are separated by a first pattern time period, each burst comprising a plurality of pulses separated by a second pattern time period, wherein the first pattern time period is greater than the second pattern time period.

* * * * *

UNITED STATES PATENT AND TRADEMARK OFFICE
CERTIFICATE OF CORRECTION

PATENT NO. : 11,298,070 B2
APPLICATION NO. : 16/616017
DATED : April 12, 2022
INVENTOR(S) : Nicholas Sinclair et al.

It is certified that error appears in the above-identified patent and that said Letters Patent is hereby corrected as shown below:

On the Title Page

Item (71), Line 1, "STIMULTATION" should be -- STIMULATION --.

At page 2, in Column 1, item (57), under "ABSTRACT", Line 8, "one of" should be -- one or --.

In the Specification

At Column 2, Line 10, "one of" should be -- one or --.

At Column 5, Line 5, "one of" should be -- one or --.

At Column 7, Line 64, "one of" should be -- one or --.

At Column 8, Line 43, "one of" should be -- one or --.

In the Claims

At Column 32, Line 19, "one of" should be -- one or --.

At Column 34, Line 27, "one of" should be -- one or --.

At Column 34, Line 43, "one of" should be -- one or --.

Signed and Sealed this
Twenty-second Day of November, 2022

Katherine Kelly Vidal
*Director of the United States Patent and Trademark Office*